United States Patent
Fink et al.

(10) Patent No.: US 10,842,373 B2
(45) Date of Patent: Nov. 24, 2020

(54) SMARTPHONE-BASED HANDHELD OPHTHALMIC EXAMINATION DEVICES

(71) Applicant: Arizona Board of Regents on Behalf of the University of Arizona, Tucson, AZ (US)

(72) Inventors: Wolfgang Fink, Tucson, AZ (US); Mark Tarbell, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/571,701

(22) PCT Filed: May 5, 2016

(86) PCT No.: PCT/US2016/030946
§ 371 (c)(1),
(2) Date: Nov. 3, 2017

(87) PCT Pub. No.: WO2016/179370
PCT Pub. Date: Nov. 10, 2016

(65) Prior Publication Data
US 2018/0153399 A1  Jun. 7, 2018

Related U.S. Application Data

(60) Provisional application No. 62/157,051, filed on May 5, 2015.

(51) Int. Cl.
*A61B 3/10* (2006.01)
*A61B 3/12* (2006.01)
(Continued)

(52) U.S. Cl.
CPC .............. *A61B 3/12* (2013.01); *A61B 3/0008* (2013.01); *A61B 3/0033* (2013.01);
(Continued)

(58) Field of Classification Search
CPC .. A61B 3/12; A61B 3/14; A61B 3/135; A61B 3/0008; A61B 3/0033;
(Continued)

(56) References Cited

U.S. PATENT DOCUMENTS 6,393,431 B1   5/2002  Salvati et al.
8,879,813 B1 * 11/2014  Solanki .................. G16H 30/20
                                            382/128
(Continued)

FOREIGN PATENT DOCUMENTS

JP     2015018244 A      1/2015
WO     2013081619 A1     6/2013
WO  WO-2013081619 A1 *   6/2013  ............... A61B 3/14

OTHER PUBLICATIONS

Chan, Jan Bond, et al. "DIY—Smartphone Slit-Lamp Adaptor." Journal of Mobile Technology in Medicine, vol. 3, No. 1, 2014, pp. 16-22. (Year: 2014).*

(Continued)

*Primary Examiner* — William R Alexander
*Assistant Examiner* — Henry A Duong
(74) *Attorney, Agent, or Firm* — Thomas Horstemeyer, LLP

(57) ABSTRACT

Various examples of methods, systems and devices are provided for ophthalmic examination. In one example, a handheld system includes an optical imaging assembly coupled to a user device that includes a camera aligned with optics of the optical imaging assembly. The user device can obtain ocular imaging data of at least a portion of an eye via the optics of the optical imaging assembly and provide ophthalmic evaluation results based at least in part upon the ocular imaging data. In another example, a method includes receiving ocular imaging data of at least a portion of an eye; analyzing the ocular imaging data to determine at least one (Continued)

ophthalmic characteristic of the eye; and determining a condition based at least in part upon the at least one ophthalmic characteristic.

26 Claims, 25 Drawing Sheets

(51) Int. Cl.
  A61B 3/00  (2006.01)
  A61B 3/135  (2006.01)
  A61B 3/14  (2006.01)
(52) U.S. Cl.
  CPC ............ *A61B 3/0041* (2013.01); *A61B 3/135* (2013.01); *A61B 3/14* (2013.01)
(58) Field of Classification Search
  CPC ... A61B 3/0041; A61B 3/1025; A61B 3/1233; A61B 3/1241; A61B 3/145
  USPC .......................................................... 351/206
  See application file for complete search history.

(56) References Cited

U.S. PATENT DOCUMENTS

| | | | | |
|---|---|---|---|---|
| 2009/0096988 | A1* | 4/2009 | Fink | ........................ A61B 3/16 351/206 |
| 2014/0350379 | A1* | 11/2014 | Verdooner | ........... A61B 5/0059 600/407 |

OTHER PUBLICATIONS

Lee, Wendy W. "Slit Lamp Adapters Turn Smartphones into Clinical Cameras." OphthalmologyWeb, May 14, 2013, www.ophthalmologyweb.com/Featured-Articles/136817-Slit-Lamp-Adapters-turn-Smartphones-into-Clinical-Cameras/. (Year: 2013).*
"What Is IPhone?—Definition from WhatIs.com." SearchMobileComputing, searchmobilecomputing.techtarget.com/definition/iPhone.Jan. 23, 2011 (Year: 2011).*
"ICloud." Apple, www.apple.com/icloud/.Oct. 6, 2011 (Year: 2011).*
International Search Report for PCT/US2016/030946 dated Jul. 20, 2016.
Chan, et al., "DIY—Smartphone Slit-Lamp Adaptor", JMTM 3:1:16-22, 2014.
"Cataracts | Causes, Symptoms, Diagnosis, Treatment, and Prevention." WebMD. WebMD, n.d. Web. 04 Oct. 23, 2016.
"Keratitis Symptoms, Causes, Treatment—What Is the Treatment for Keratitis? MedicineNet." MedicineNet. N.p., n.d. Web. Feb. 23, 2015.
"Laser Safety." Wikipedia. Wikimedia Foundation, n.d. Web. Feb. 16, 2015.
"Managing Retinal Injuries From Lasers." Managing Retinal Injuries From Lasers. N.p., n.d. Web. Mar. 20, 2016.
"Neuroptics—Home." Neuroptics—Home. N.p., n.d. Web. Feb. 13, 2015.
Duda, R. O. and Hart, P. E., "Use of the Hough Transformation to Detect Lines and Curves in Pictures". Communications of the AMC. (Jan. 1972) vol. 15 No. 1; p. 11-15.
Zhu, D. Moore, S. T., and Raphan, T., "Robust Pupil Center Detection Using a Curvature Algorithm". Computer Methods and Programs in Biomedicine. (Nov. 1998) vol. 59 ; p. 145-157.
Masi, M. G., Peretto, L., and Tinarelli, R., "Measurement of the Pupil Diameter Under Different Light Stimula". International Instrumentation and Measurement Technology Conference. (May 2009) 5 pages.
Johnson, W. R., et al. "Snapshot Hyperspectral Imaging in Ophthalmology". Journal of Biomedical Optics. (Jan./Feb. 2007) vol. 12 Issue. 1; 7 pages.
Brackbill, R. M., et al. "Surveillance for World Trade Center Disaster Health Effects Among Survivors of Collapsed and Damaged Buildings". Surveillance Summaries; MMWR. (Apr. 2006) vol. 55, No. SS-2; p. 1-18.
Xu, C. and Prince, J. L. "Active Contours, Deformable Models, and Gradient Vector Flow". (http://www.iacl.ece.jhu.edu/static/gvf/).
Kass, M., Witkin, A. and Terzopoulos, D. "Snakes: Active Contour Models". International Journal of Computer Vision. (Jan. 1988) p. 321-331.
Carlson N. B., Kurtz D. "Clinical Procedures for Ocular Examination". New York, McGraw Hill (Apr. 2004). 487 pages.
McManus, J., et al. "Teleconsultation Program for Deployed Soldiers and Healthcare Professionals in Remote and Austere Environments". Prehospital and Disaster Medicine. (May/Jun. 2008) vol. 23, No. 3; p. 210-216.
Poropatich, C. R. K., et. al. "The U.S. Army Telemedicine Program: General Overview and Current Status in Southwest Asia" TeleMedicine and e-Health. (Aug. 2006) vol. 12, No. 4; p. 396-408.
Mines, M. J., et al. "The United States Army Ocular Teleconsultation Program 2004 through 2009". American Journal of Ophthalmology. (Jul. 2011) vol. 152; p. 126-132.
Mines, M. J., et al. "Ocular Injuries Sustained by Survivors of the Oklahoma City Bombing". American Academy of Ophthalmology. (May 2000) vol. 107, No. 5; p. 837-843.
Ehlers J. P. and Shah C.P.. "The Wills Eye Manual Office and Emergency Room Diagnosis and Treatment of Eye Disease" Philadelphia (Nov. 2008) Fifth Edition. 455 pp.

\* cited by examiner

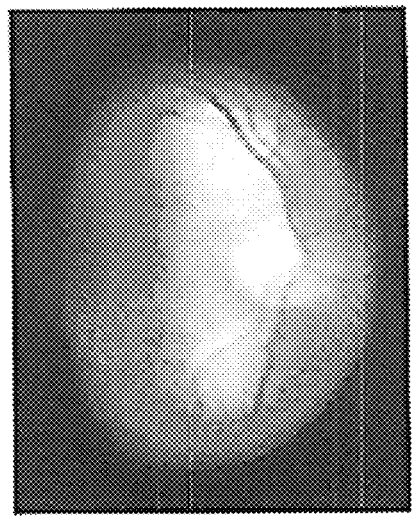
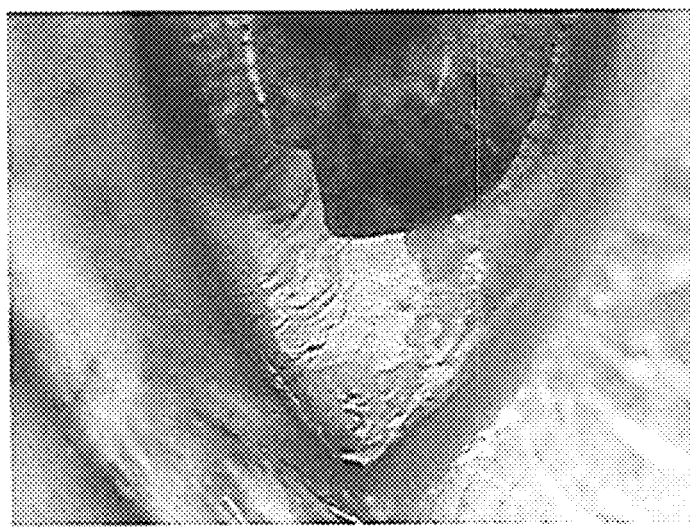
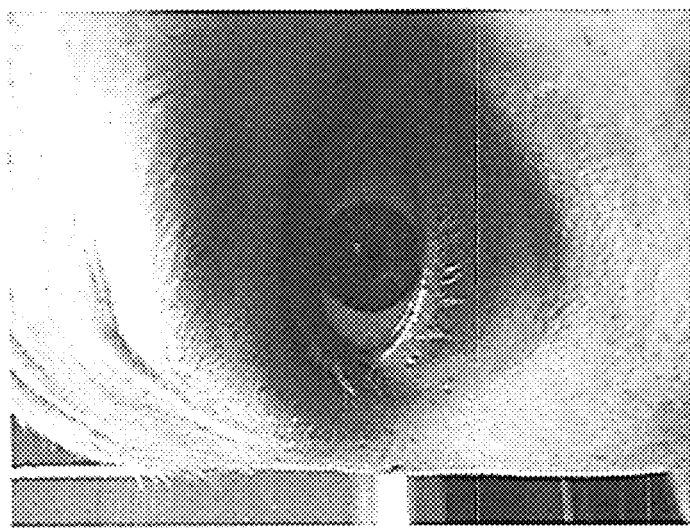
Fig. 1: (L) raw iPhone camera image of eye; (M) using 4X lens; (R) fundus image using ophthalmoscope optics in front of iPhone camera.
FIG. 1

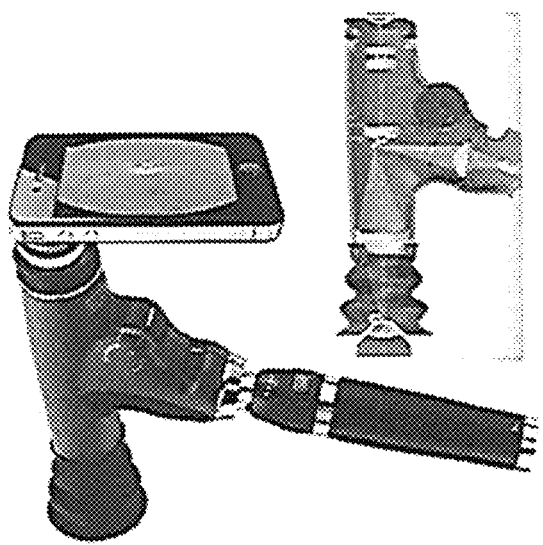
Fig. 2: Proposed smartphone-based ophthalmic microscope
FIG. 2
Fig. 3: Proposed smartphone-based ophthalmic slit lamp.
FIG. 3
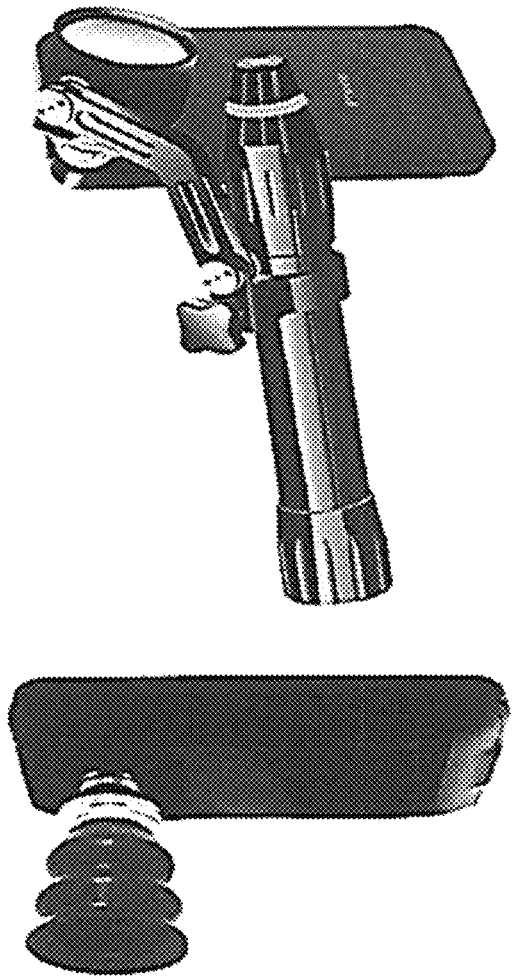
Fig. 4: Proposed smartphone-based ophthalmoscope with eyecup, and example optical layout.
FIG. 4

Eidolon Hand Held Slit Lamp Model 510L

The ultraportable Model 510L is a popular diagnostic instrument for examination of anterior segment structures and ocular abnormalities. Its patented optical system produces a high-brightness, continuously adjustable slit image. Ideal wherever a tabletop slit lamp is impractical or unavailable, the Model 510L is particularly suited for pediatric and geriatric settings, emergency departments, screenings, ward rounds, bedside examinations, post-op evaluations, and mission work.

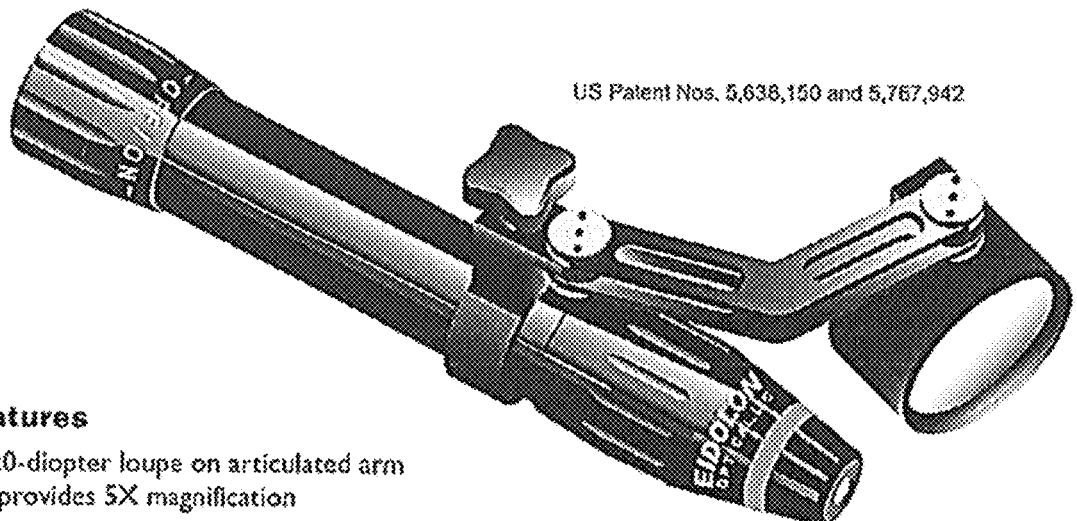

US Patent Nos. 5,638,150 and 5,767,942

Features
- 20-diopter loupe on articulated arm provides 5X magnification
- Ultraportable, weighs only a few ounces
- Wide field of view, outstanding image quality
- Operates for hours on standard alkaline AA batteries
- Gravity-independent for use at bedside
- New ballistic nylon soft pouch case included
- Unconditional 5-year guarantee
- Made in USA $ 495.00

Accessories
- Optional cobalt blue filter for examinations with fluorescein
- High-resolution Digital Camera with Eidolon Adapter
- Hard-shell case

FIG. 6B

*One mirror, one lens, one camera*

*Two mirrors, one lens, one camera*

Hinged angled mirrors, with stereo axis convergence.　　Displaced mirrors. No stereo axis convergence.

*Two angled mirrors, one camera*

*Two angled mirrors, one plane mirror, one camera*

*Two angled mirrors, one plane mirror, one camera, symmetric arrangement*

*Four mirrors, one lens, one camera*

Theodore Brown's Stereophotoduplicon, 1894
FIG. 9E (Cont.)
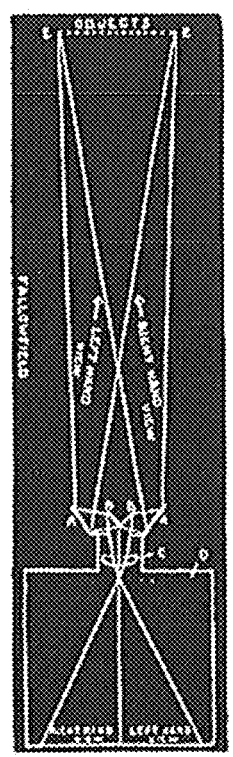
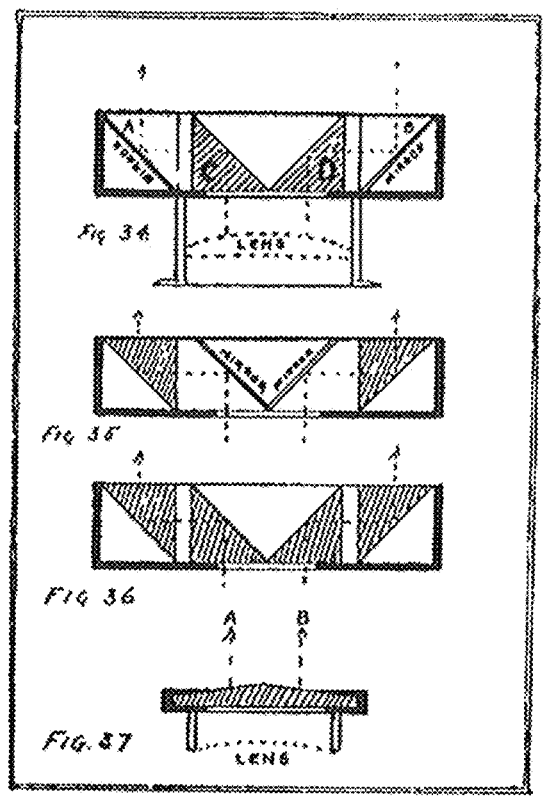
*For 3D microscopy in particular: optical modulator switch*
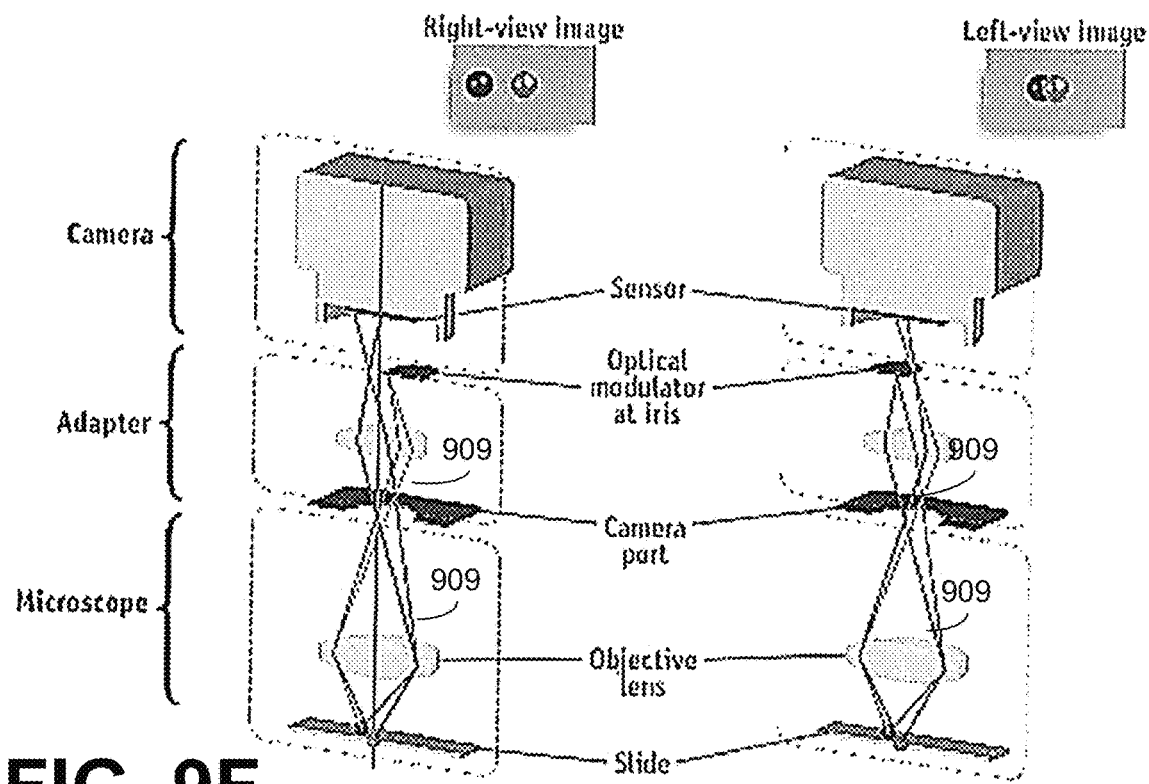
FIG. 9F

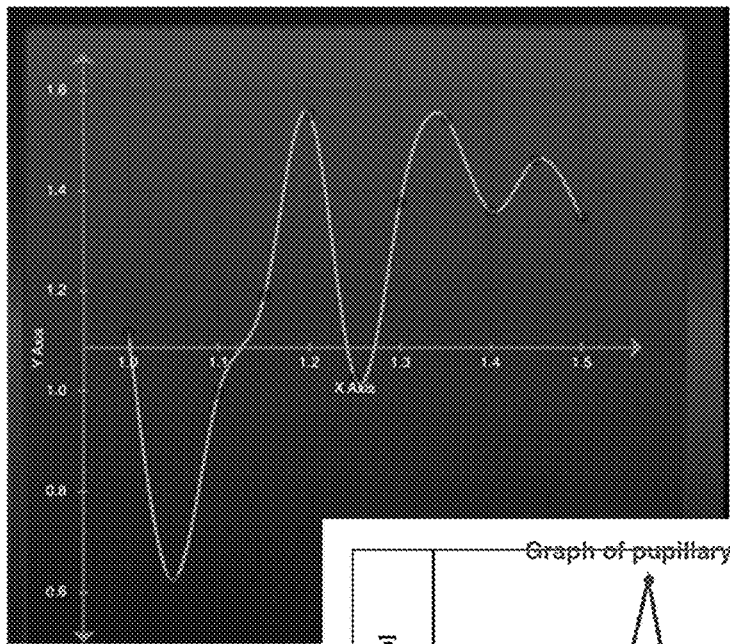

FIG. 15A

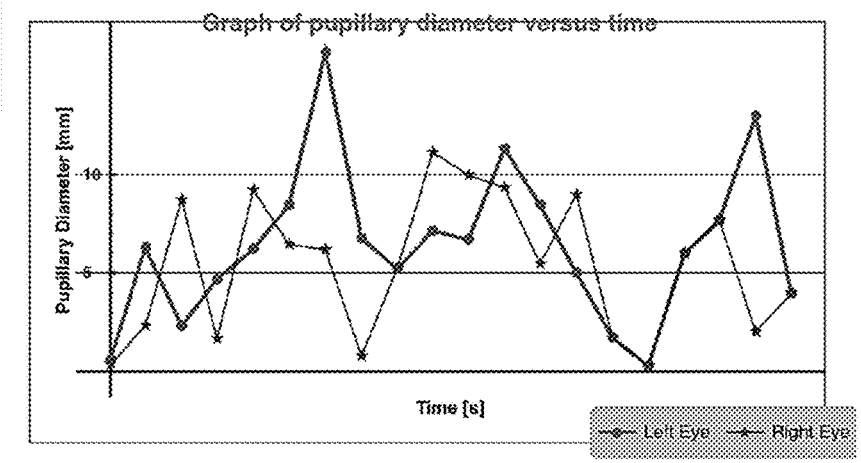

FIG. 15B

| Test Number | Test Description | Requirements |
|---|---|---|
| 1 | App will be started from iPhone. User will select recording type (photo/video capture) Enter parameters for duration of capture and data transfer. | Use of iPhone 5S for photo and video capture iOS platform. |
| 2 | With programmed delay, user will insert phone in headset. After capture, app transfers data to server. | 1280 x 720 capture. |
| 3 | App graphs result from remote server | Graph result as function of pupillary diameter variation with respect to time |

FIG. 16

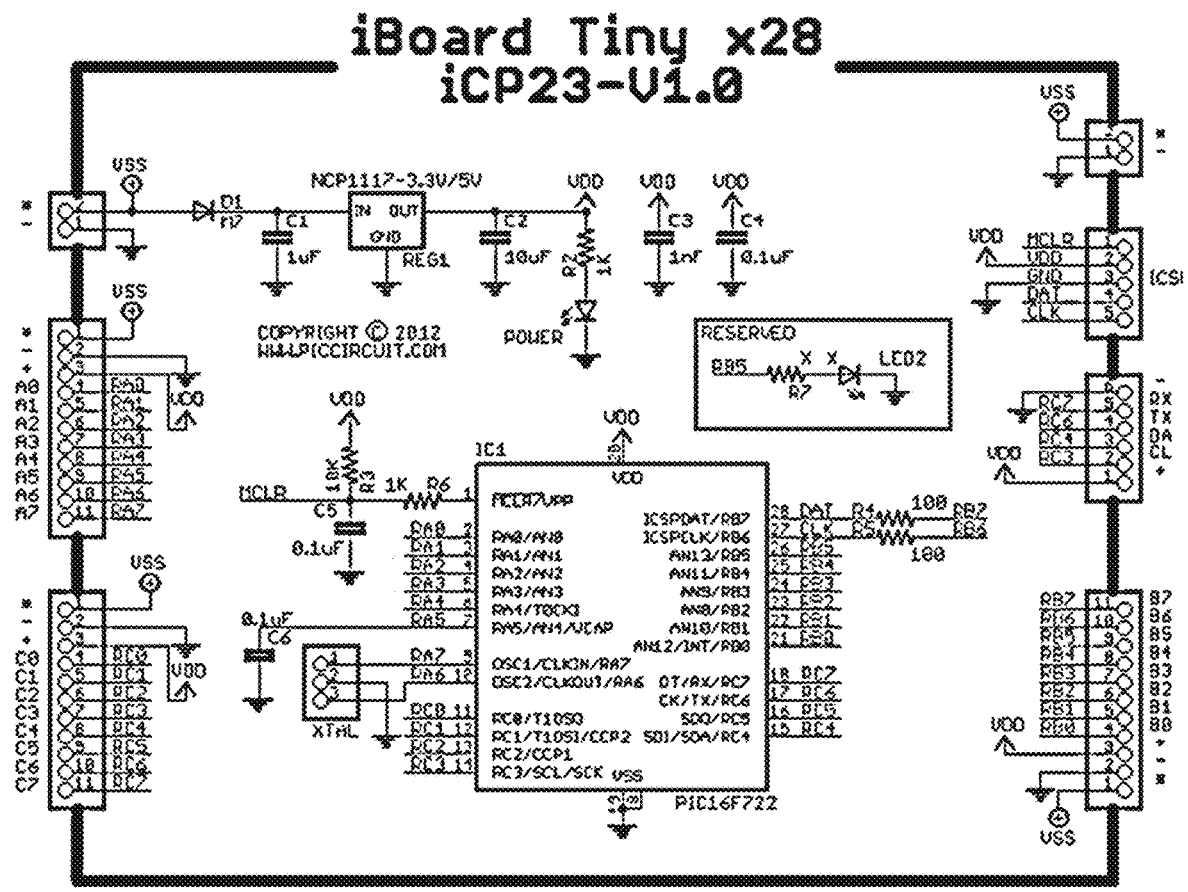
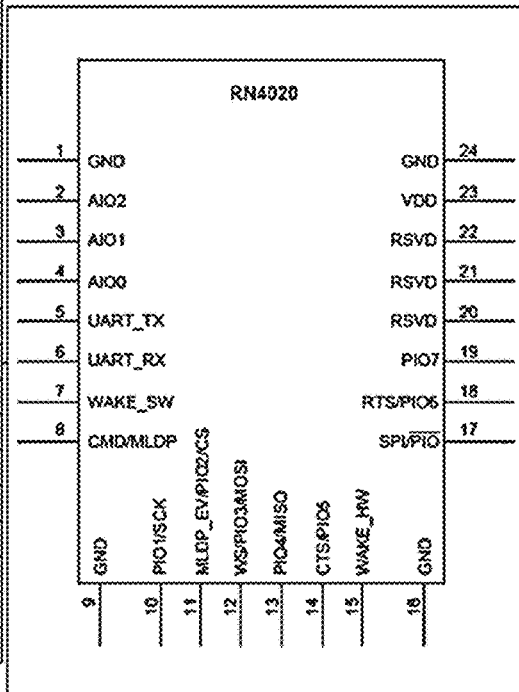
FIG. 18B

SMARTPHONE-BASED HANDHELD OPHTHALMIC EXAMINATION DEVICES

CROSS REFERENCE TO RELATED APPLICATIONS

This application is the 35 U.S.C. § 371 national stage application of PCT Application No. PCT/US2016/030946, filed May 5, 2016, which claims priority to, and the benefit of, U.S. provisional application entitled "SMARTPHONE-BASED HANDHELD OPHTHALMIC EXAMINATION DEVICES" having Ser. No. 62/157,051, filed May 5, 2015, both of which are herein incorporated by reference in their entireties.

STATEMENT REGARDING FEDERALLY SPONSORED RESEARCH OR DEVELOPMENT

This invention was made with government support under Grant No. IIP1430062, awarded by NSF, and Grant No. R25 EB012973, awarded by NIH. The Government has certain rights in the invention.

BACKGROUND

Ocular trauma is a significant cause of preventable visual impairment. Ocular injuries can account for up to a third of the casualties sustained by workers in hazardous or disaster environments; while untold others can experience other less devastating eye issues while on the job. Because the diagnosis and treatment of ocular trauma and disease are daunting to most non-ophthalmic providers, most opt to refer ocular patients to local medics, ophthalmologists, or optometrists for evaluation of all but the most routine conditions. However, the presence of such professionals may be very limited or non-existent in certain scenarios so that transferring even relatively simple ocular conditions entails significant risk, or may not be possible at all (e.g., remote sites, disaster areas, military environments, ships at sea or humanitarian endeavors). In this regard, telediagnosis offers the potential of both rapidity of evaluation and increased security; evacuation of the patient can then be more judiciously advised—or avoided—based on evaluation of the tele-information.

SUMMARY

Embodiments of the present disclosure are related to ophthalmic examination. Ophthalmic examination devices and systems can include, but are not limited to, a smartphone-based ophthalmic microscope or ophthalmoscope, ophthalmic slit lamp, pupillometer, fundoscope, stereo imaging device, hyperspectral camera, and a Scheimpflug camera.

In one embodiment, among others, a handheld ophthalmic examination system comprises an optical imaging assembly coupled to a user device comprising a camera aligned with optics of the optical imaging assembly. The user device can be used to: obtain ocular imaging data of at least a portion of an eye via the optics of the optical imaging assembly, and provide ophthalmic evaluation results based at least in part upon the ocular imaging data. In another embodiment, a method for ophthalmic examination comprises receiving ocular imaging data of at least a portion of an eye, the ocular image provided by an ophthalmic examination device; analyzing the ocular imaging data to determine at least one ophthalmic characteristic of the eye; and determining a condition of a subject based at least in part upon the at least one ophthalmic characteristic. The ocular imaging data can be received and analyzed by a computing device or by the user device (e.g., a smartphone).

In one or more aspects of these embodiments, the user device can be a smartphone. The ophthalmic examination device can be a smartphone-based handheld ophthalmic examination device. The ophthalmic examination device can comprise an optical imaging assembly. The optical imaging assembly can comprise a light source configured for ophthalmoscopic examination of the eye. The ophthalmic examination system or device can comprise a slit lamp, wherein the optics are configured for slit lamp examination of the eye. The optical imaging assembly can comprise the optics and a light source configured for pupillometer examination of the eye. The optical imaging assembly can comprise the optics and a light source configured for fundoscope examination of the eye. The optical imaging assembly can comprise the optics and a light source configured for Scheimpflug camera imaging of the eye. The optical imaging assembly can comprise the optics and a light source configured for stereo imaging of the eye. The optical imaging assembly can comprise the optics and a light source configured for microscopic examination of the eye. The optical imaging assembly can comprise the optics and a light source configured for hyperspectral camera imaging of the eye.

In one or more aspects of these embodiments, the ocular imaging data can include an ocular image. The ophthalmic evaluation results can be based at least in part upon a portion of the ocular image. The user device or ophthalmic examination device can be configured to obtain a plurality of ocular images. The ophthalmic evaluation results can be based at least in part upon a portion of the plurality of ocular images. The plurality of ocular images can be a series of ocular images. In one or more aspects of these embodiments, the series of ocular images can be in form of a video or movie. The user device or ophthalmic examination device can be configured to provide the ocular image to a computing device for processing and ophthalmic evaluation of the ocular image and receive the ophthalmic evaluation results from the computing device. The user device or ophthalmic examination device can provide the ocular image to the computing device via a wireless network link. The wireless network link can be a cellular data link. The computing device can be a remotely located server (e.g., a cloud computing server). The optical imaging assembly can be detachably affixed to a casing coupled to the user device or ophthalmic examination device. The user device or ophthalmic examination device can be configured to process the ocular image.

In one or more aspects of these embodiments, the evaluation results can be provided to the user device or ophthalmic examination device for rendering. The evaluation results can be based at least in part upon the at least one ophthalmic characteristic. The ocular image data can comprise images of both eyes of the subject. The ocular image data can comprise an image or a video of at least a portion of the eye.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 includes examples of ocular images according to various embodiments of the present disclosure.

FIGS. 2-4 are examples of various smartphone-based handheld ophthalmic examination devices according to various embodiments of the present disclosure.

FIGS. 6A through 6E illustrated examples of various smartphone-based slit lamps according to various embodiments of the present disclosure.

FIGS. 9A through 9F illustrate examples of a smartphone-based stereo imaging according to various embodiments of the present disclosure.

FIGS. 15A and 15B are examples of information provided by the smartphone application according to various embodiments of the present disclosure.

FIG. 16 illustrates an example of operation of the smartphone application according to various embodiments of the present disclosure.

FIGS. 17, 18A and 18B illustrate components of the smartphone-based examination device according to various embodiments of the present disclosure.

DETAILED DESCRIPTION

Figure 5:
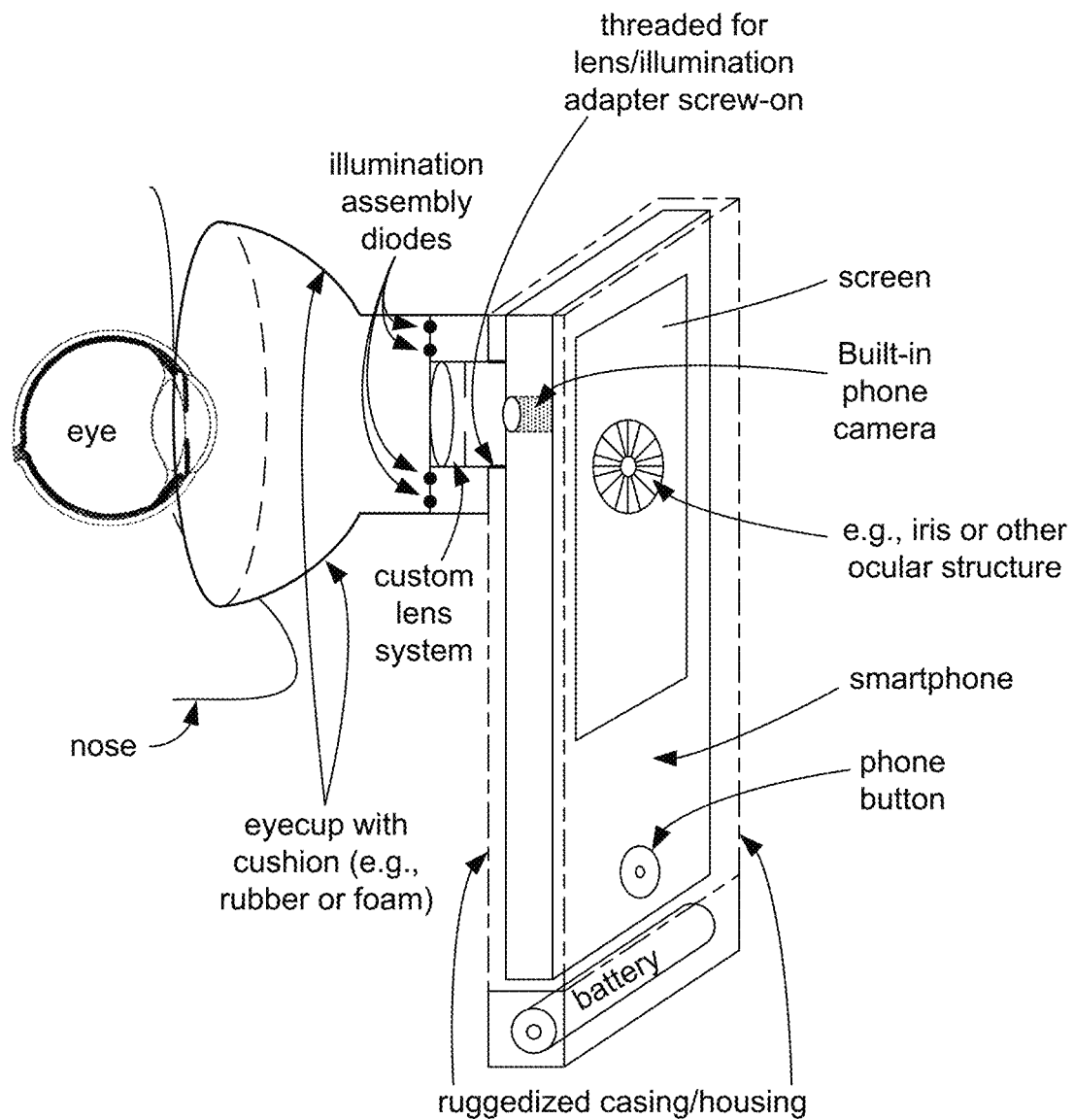
FIG. 5 illustrates an example of a smartphone-based microscope/ophthalmoscope according to various embodiments of the present disclosure.

Disclosed herein are various embodiments related to ophthalmic examination devices such as, but not limited to, a smartphone-based ophthalmic microscope or ophthalmoscope, ophthalmic slit lamp, pupillometer, fundoscope, stereo imaging device, hyperspectral camera and/or a Scheimpflug camera. Reference will now be made in detail to the description of the embodiments as illustrated in the drawings, wherein like reference numbers indicate like parts throughout the several views.

This disclosure presents technology that can be extended to other applications, such as, but not limited to, pupillometry, glaucoma testing, screening for retinal detachment, Scheimpflug imaging, hyperspectral imaging, and stereo imaging. This may be implemented by a plug-and-play architecture that allows rapid and easy selection of the various ophthalmic examination modalities (e.g., microscope, slit lamp, and ophthalmoscope). An ophthalmic microscope can be used to perform high-resolution microphotography of the surface of the eye (e.g., scleral, corneal imaging). An ophthalmic slit lamp can be used to perform high-resolution photography of internal ocular structures such as the anterior chamber and crystalline lens. An ophthalmoscope can be used to perform high-resolution photography of the fundus, i.e., retina of the eye. The disclosed ophthalmic examination device can allow the user to locally assess the images taken with the smartphone's built-in camera. Moreover, to provide in-depth analysis, it can be equipped with a server-based telediagnostic analysis capability, such as image segmentation of the fundus to identify vessels. The results of such analyses can be sent back to the originating user device (e.g., smartphone or tablet). At least two major markets can be addressed: (1) the professional medical market, such as paramedics, medics, optometrists, and ophthalmologists; and (2) the military market, as evidenced by the recent Army SBIR Call "Adapting Smart-Phones for Ocular Diagnosis."

Because ophthalmology is so heavily reliant to visual information, high-quality photographs and other source material are very helpful to the teleconsultants. Limitations to current photodocumentation are the 2-dimensional nature of standard photographs, the inability to selectively focus standard cameras on the microscopic structures of the ocular anatomy on which diagnoses can hinge, and overall resolution. Because of their size, weight, cost, fragility, and training requirements, conventional and portable ophthalmic examination devices (e.g., microscopes, slit lamps, and ophthalmoscopes) are not typically deployed in field clinical settings such as remote sites, military environments, ships' sick bays, disaster areas, or humanitarian missions, and even when such equipment is made available, they are generally without a photographic capability.

Smartphone technology has recently put high quality photography, advanced processing capability, and robust connectivity into the hands of technically untrained populations. Still photos or video can be captured and quickly edited for rapid dispatch via the Internet, in near real-time, or can be stored for later transmission. Continual advances in smartphone and tablet hardware have increased photographic resolution while decreasing the size of the cameras.

Such handheld capability is of significant interest to field ophthalmology. Portability, connectivity, and affordability would allow use by minimally trained personnel and deployment to areas heretofore considered inaccessible or impractical. Fortunately, state-of-the-art optical extension of existing smartphones may answer most of the specialty's needs. For example, a key aspect would be the capability to do high-resolution photography of ocular structures that vary in scale from a few centimeters (external macro photography), to millimeters (microphotography of the surface of the eye), to sub-millimeter or microns (e.g., internal structures such as the anterior chamber, lens, and fundus). Additionally, selective illumination by slit beams of light cast at oblique angles allows greater precision in diagnosis unavailable in current smartphone technology.

Software applications can facilitate ophthalmic telediagnosis, including collection of patient ocular exam data as well as enhanced photography/videography and bundling for teleconsultation. This capacity would include both real-time and store-and-forward teleconsultation, in addition to utilizing powerful (server-based) backend processing to render analysis of the collected data in near real time with potential transmission back to the originating smartphone.

A smartphone-based handheld ophthalmic examination device is disclosed that is adaptive (via a customized lens adapter) for ophthalmic instruments, such as, but not limited to:

Ophthalmic Microscope: performing high-resolution microphotography of the surface of the eye;

Ophthalmic Slit Lamp: performing high-resolution photography of internal ocular structures such as the anterior chamber and lens;

Ophthalmoscope: performing high-resolution photography of the fundus;

Also as a pupillometer, fundoscope, stereo imaging device, hyperspectral camera, or a Scheimpflug camera.

Such an ophthalmic examination device can allow the user to locally assess the images taken with the smartphone's built-in camera.

Moreover, to provide the capability for in-depth ophthalmic analysis, the device can be equipped with a server-based telediagnostic analysis capability, where images taken with the smartphone-based ophthalmic examination device can be transmitted via a network such as the Internet to a server, which performs a set of predefined analyses. The results of the analyses will be sent back the originating device. As an example, the analysis can apply a standard image segmentation algorithm to identify vessels in the fundus.

Preliminary research has indicated feasibility of the smartphone-based handheld ophthalmic examination device. FIG. 1 shows (1) an example of a raw image taken with a default iPhone camera (left (L) image), (2) a four times magnified image of the temporal sclera and parts of the iris (middle (M) image) of the eye in the left image using a 4× magnification lens in front of the camera, and (3) an image of the fundus (right (R) image) of the same eye using a handheld ophthalmoscope optic in front of the iPhone camera.

The smartphone-based handheld ophthalmic examination device with be discussed including various adaptations (e.g., microscope, slit lamp, and ophthalmoscope) that enable field-conducted examinations that are otherwise restricted to clinical settings (e.g., medical offices and clinics). Compared to state-of-the-art ophthalmic equipment, the smartphone-based device can be miniaturized, portable, and usable by non-specialists (e.g., with a low training requirement) outside a clinical setting. Furthermore, it is extensible to other applications, such as pupillometry, glaucoma testing, screening for retinal detachment, Scheimpflug imaging, hyperspectral imaging, and/or stereo imaging. This can be made possible by the plug-and-play architecture (e.g., via customized lens adapter on the smartphone casing) that allows rapid and easy selection of the various ophthalmic examination modalities (e.g., microscope, slit lamp, ophthalmoscope, etc.).

Server-based telediagnostic analysis capability allows for either tele-expert or automated machine-based in-depth evaluation of the submitted image data. This is possible because smartphones are ubiquitous and Internet-connected. This capability enables both real-time teleconsultation and store-and-forward teleconsultation that can be assessed later in time when convenient or possible.

The smartphone-based ophthalmic microscope, slit lamp, and/or ophthalmoscope can be implemented using, for example:

A smartphone such as, but not limited to, an Apple iPhone 5.

The iPhone built-in, rear-facing high-resolution (e.g., 8 MP) digital camera can be used as the imaging baseline for all three ophthalmic examination devices. The user can monitor on the actual phone screen what the camera is seeing. This enables accurate targeting of areas of interest, such as ocular surfaces (e.g., cornea), structures within (e.g., crystalline lens, fundus), and cavities (e.g., anterior chamber and vitreous cavity).

The iPhone camera auto-focusing mechanism can be manually directed to the areas of interest within the camera image.

Both macroscopic and microscopic imaging of ocular surfaces and structures inside the eye can be accomplished by mounting appropriate magnification lenses or entire optical systems via a customized lens adapter onto a customized phone casing. An example of the microscope is shown in FIG. 2, of the slit lamp is shown in FIG. 3, and of the ophthalmoscope is shown in FIG. 4.

To determine the needed lens and optical systems, respectively, and to determine their positioning relative to the iPhone camera, an optical test bed can be established with micrometer-accuracy positioning. Preliminary tests have shown that such precision will be needed for optimal optical alignment.

Images obtained with any of the above ophthalmic examination devices can be stored on the iPhone and can be subsequently analyzed and evaluated on the iPhone itself. In various embodiments, the ocular image data can be processed and evaluated on the user device (e.g., the smartphone), e.g., by utilizing a built-in graphical processing unit (GPU) or general-purpose graphical processing unit (GGPU). For fully automated telediagnosis (e.g., in-depth analyses), a bidirectional data transfer between an iPhone and a server backend can be implemented (e.g., via the Internet) as follows:

An iPhone user can take a snapshot with built-in camera or select a previously taken image.

The iPhone can then submit the image data to the server over, e.g., the Internet or a cellular data connection.

The server receives the image and runs an analysis program on the image data such as a custom analysis program (e.g., an image segmentation algorithm).

The server can generate end data products based upon the analysis (e.g., a segmented image).

The server can then return the processed image and analytic data products to the requesting iPhone.

The iPhone then receives and displays the processed image and analytic data products to the user.

Figure 10A:
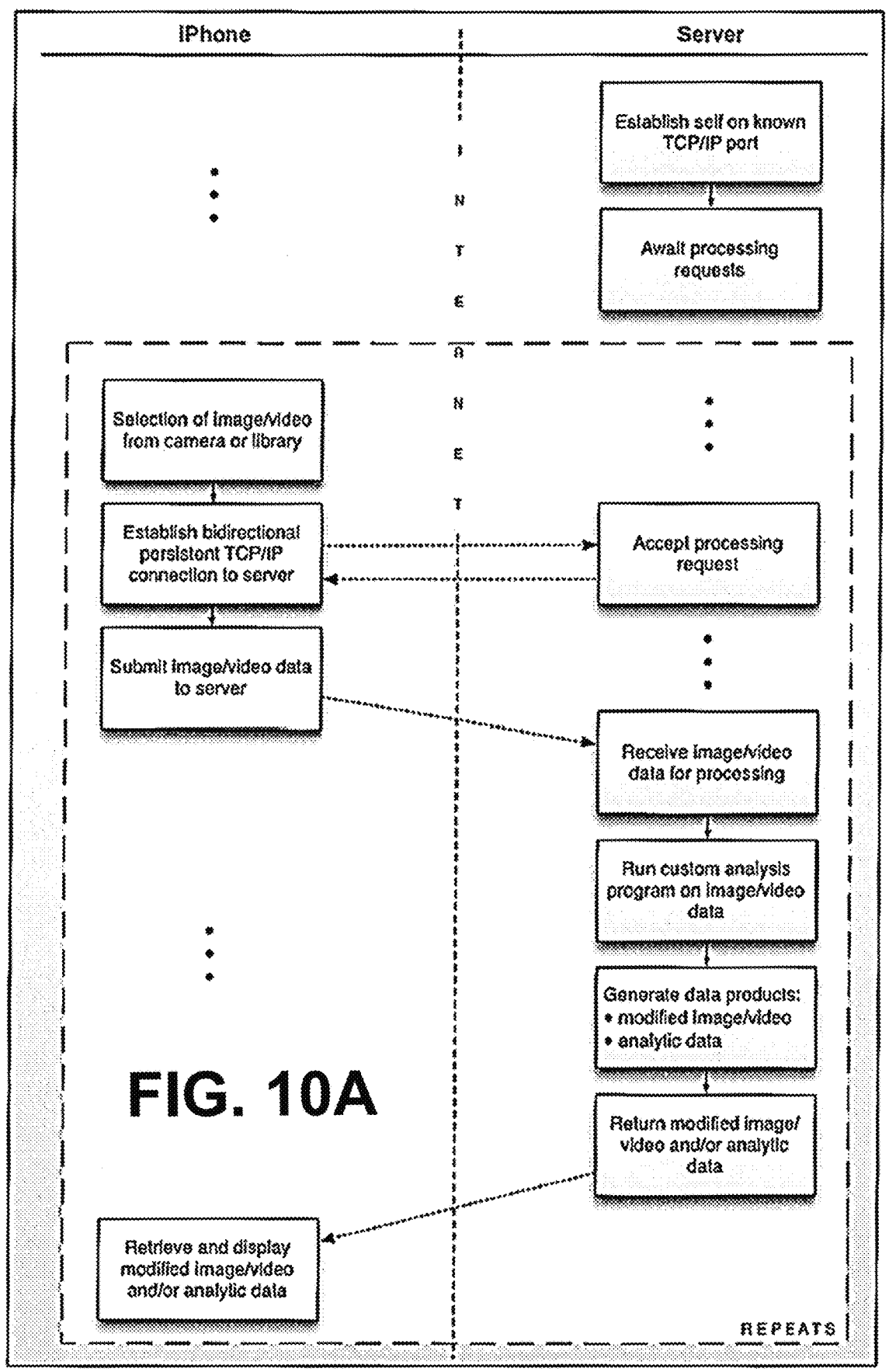
FIGS. 10A and 10B are flow charts illustrating examples of smartphone-server backend interaction according to various embodiments of the present disclosure.
Figure 10B:
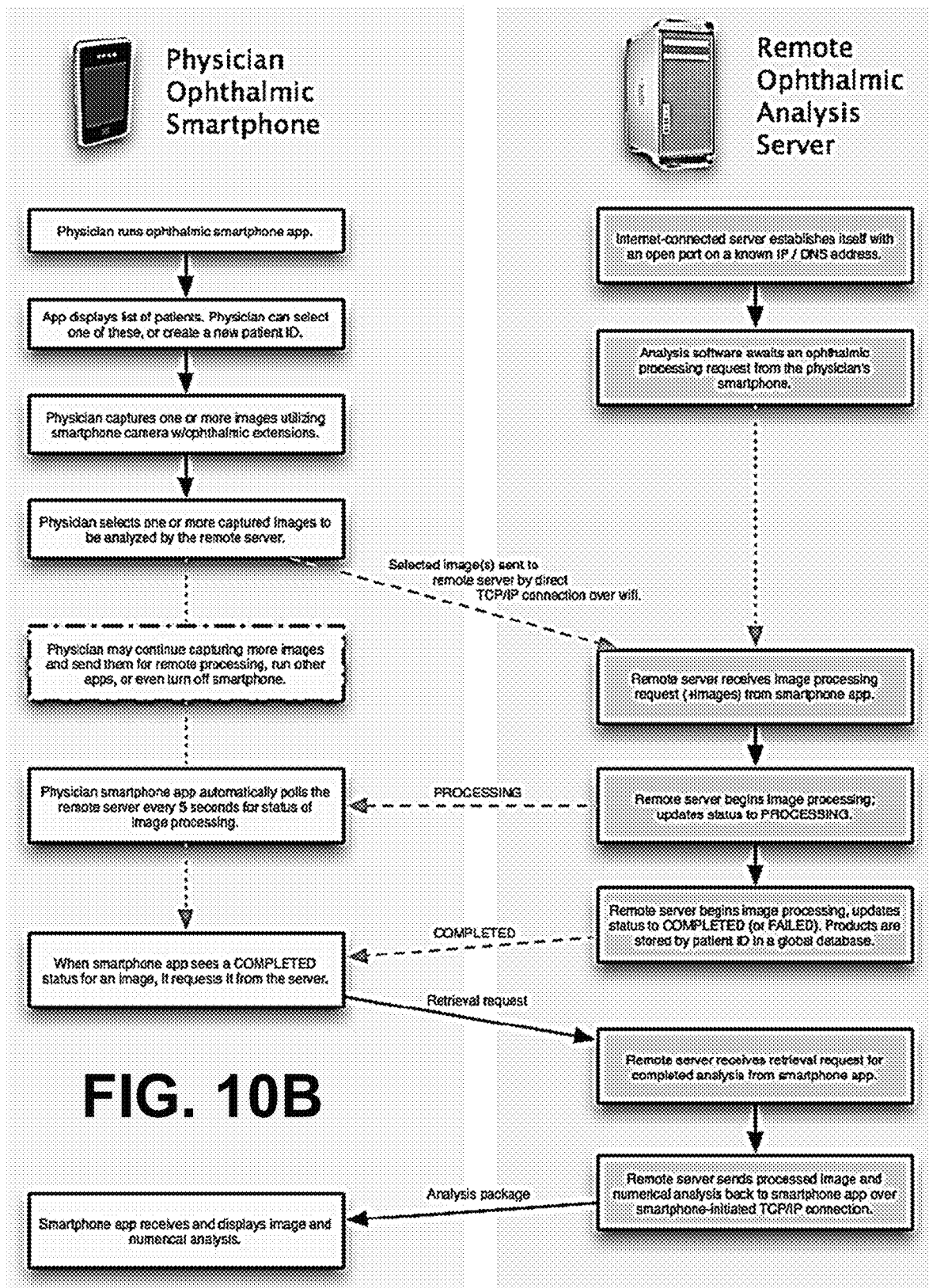

FIGS. 10A and 10B illustrate examples of smartphone-server backend interactions as will be discussed below.

The smartphone-based handheld ophthalmic examination device can provide capabilities such as:

High-resolution microphotography of the surface of the eye (e.g., sceral, corneal imaging);

High-resolution photography of internal ocular structures such as the anterior chamber and lens;

High-resolution photography of the fundus;

Server-based telediagnosis: analysis of wirelessly transmitted imagery (via the Internet) and transmission of analysis data back to the originating smartphone;

Portability and field-deployability through miniaturization; and

Usability by non-specialists (with a low training requirement) outside a clinical setting;

Pupillometer examination, fundoscope examination, stereo imaging, and/or hyperspectral imaging.

The smartphone-based device can be extended to include other applications such as, e.g., pupillometry, glaucoma testing, screening for retinal detachment, Scheimpflug imaging, and stereo imaging. A plug-and-play architecture also allows for rapid and easy selection between the various ophthalmic examination modalities (e.g., microscope, slit lamp, and ophthalmoscope).

The smartphone-based ophthalmic examination device may also be considered a product of a new and emerging field called Mobile Health or (M-Health). Mobile Health is the intersection of mobile technology and healthcare, m-health and tele-health are deeply intertwined and share the possibility of reshaping how and where healthcare is delivered. M-health is an emerging field characterized by the use of portable, mobile devices capable of collecting, storing, retrieving, and transmitting data over wireless networks in real time for the purpose of improving safety and quality of care. The concept of m-health centers on how to decentralize healthcare so that effective decisions can be made where patients are located. M-health includes a provider component in addition to its application in home tele-health systems. In tele-health systems, mobile phones or PDAs with wireless networking capabilities may serve as gateways that process, store, and transfer measured parameters to clinicians for further analysis or diagnosis.

Additionally, there is particular interest in how m-health can improve access to care in developing countries. Worldwide more than 2 billion mobile phones are in use. In developing nations where there is a shortage of both funds and trained medical technicians, m-health makes it easier for healthcare practitioners to communicate and for illiterate patients to access health information using their mobile phones. The success of m-health and tele-health are inextricably related. As mobile penetration increases and large cellular carriers continue to explore additional applications for growth and partner outside of their industry, large growth potential is expected for the emerging m-health market.

There is great potential for ocular diagnosis in arenas outside the hospital setting. An entire ocular diagnosis and monitoring segment of M-health can be established with the smartphone-based ophthalmic examination device. By bringing the examination equipment to the patient rather than bringing the patient to the examination equipment, it is possible to bring healthcare to individuals who may not otherwise have access. This can form a governing principle to the development of this and other examination equipment.

With the smartphone-based ophthalmic examination device, not only can information regarding ocular diagnosis be acquired, but it can be communicated to other health professionals for a full diagnosis. This device will benefit from the growth of the Telemedicine Technologies. Telemedicine, which is the use of telecommunications technology to deliver medical information or services to patients or other users at a distance from the provider, is a rapidly growing field of clinical medicine. For example, telemedicine can be utilized in many combat and disaster scenarios.

Ocular injuries currently account for approximately 13-22% of all combat casualties and up to 32% in disaster scenarios, while untold others experience other less devastating eye issues while deployed. Because the diagnosis and treatment of ocular trauma and disease are daunting to most non-ophthalmic providers, most opt to refer ocular patients to theater ophthalmologists or optometrists for evaluation of all but the most routine conditions; most often, however, those assets are very limited or non-existent in military operations so that transferring even relatively simple ocular conditions entails significant risk, or may not be possible at all (e.g., ships afloat or humanitarian missions).

In this regard, telediagnosis should offer both rapid evaluation and increased security; evacuation of the patient can then be more judiciously advised, or even avoided, based on evaluation of the tele-information. Because Ophthalmology is so heavily reliant on visual information, high-quality photographic attachments are very helpful to the teleconsultants. Limitations to current photodocumentation are the 2-dimensional nature of standard photographs, the inability to selectively focus standard cameras on the microscopic structures of the ocular anatomy on which diagnoses can hinge, and overall resolution. Because of their size, weight, cost, fragility, and training requirements, conventional and portable slit lamps are not typically deployed hi all forward clinical settings such as ships' sick bays, Forward Operating Bases (FOBs), Battalion Aid Stations (BAS), disaster areas, or humanitarian missions, and when available are not equipped with photo capability (a technique that requires considerable skill in itself).

Smartphone technology has made high quality photography, advanced processing capability, and robust connectivity available to a wide range of individuals. Still photos or video can be captured and quickly edited for rapid dispatch via, e.g., the internet in near real-time, or can be stored for later transmission. Smartphone hardware has increased photographic resolution and even allows for 3-D applications. The portability, connectivity, and affordability of smartphones allow for the use in and deployment to areas heretofore considered inaccessible or impractical (e.g., ophthalmic healthcare in military settings). The capability to do high-resolution stereo photography of ocular structures that vary in scale from a few centimeters (external macro photography), to millimeters (microphotography of the surface of the eye), to sub-millimeter or microns (e.g., internal structures such as the anterior chamber, lens and fundus) offers flexibility that may be important. Additionally, selective illumination by slit beams of light cast at oblique angles can allow for greater precision in diagnosis.

Software applications should facilitate ophthalmic telediagnosis, to include collection of patient ocular exam data as well as enhanced photography/videography and bundling for teleconsultation. The capacity can include both real-time and store-and-forward teleconsultation.

The disclosed ocular telediagnostic tool can be used by minimally trained providers in remote, austere, or isolated environments such as military forward operating bases, ships afloat and away from port, or on humanitarian missions and in disaster zones where medical infrastructure and capability is reduced or nascent. In addition, the ocular telediagnostic tool can be used to facilitate triage processes in these and other situations. Development of a smartphone-based ophthalmic slit lamp (or slit lamp system) would allow high-quality telemedicine consultations with ophthalmologists and optometrists, thereby potentially providing on-site diagnosis and treatment capability, and probably avoiding evacuation and minimizing security risks. Beyond military interest, commercial interest could include disaster readiness organizations as well as humanitarian-relief organizations, and would not be limited to ocular diagnostics. Teleconsultation software applications could be attractive to other medical specialties, e.g., skin cancer detection. Additionally, advanced and stereophotographic capabilities could be attractive to the general public.

Construction of a general-purpose ophthalmic examination device, and in particular a smartphone-based (bio-) microscope or ophthalmoscope, slit lamp, pupillometer, fundoscope, Scheimpflug camera, hyperspectral imaging device, and/or stereo imaging device are disclosed. Functional features that can be implemented using the smartphone-based ophthalmic examination device include, but are not limited to:

The ability to capture high quality 2-dimensional and stereo-photography (and/or videography) of the eye(s) and adnexa;

The ability to transmit bundled examination data and photo information as near-real-time, or store-and-forward;

The ability to focus at different physical scales, from macro- (e.g., single eye or both; eyelids; adnexa; and gross ocular structures), to micro- (e.g., cornea, iris, lens, fundus etc.) and sub-millimeter-scales, potentially including micron-scale (e.g., corneal epithelium, anterior chamber cells, etc.);

The ability to focus principally on external and anterior internal ocular structures (e.g., lids, conjunctiva, sclera, cornea, etc.) with flexibility to image deeper internal ocular structures (e.g., lens, fundus, optic nerve);

The ability to select lighting and illumination patterns from various direct or oblique angles, including, but not limited to, broad or diffuse beams, slit-beams, and pencil beams of light;

The ability to select from various illumination colors and wavelengths, such as (but not limited to) white, cobalt blue, red-free, ultraviolet, and infrared lights;

Modular adaptability for use in a variety of platforms and configurations, such as freehand-operated, to stabilized-handheld (e.g., a portable slit lamp platform), to table-mounted (e.g., a conventional slit lamp platform);

The adaptability to use in a variety of settings and environments, such as first-responder/casualty-side in a field setting; bedside; or fixed facility/clinic/sick bay;

The adaptability to use in a variety of climatic conditions, such as extremes of heat and humidity, dust, rain, altitude, barometric pressure, etc.;

Robust physical ruggedness to survive physical activities and abuses common to and expected of a combat, disaster, or otherwise austere environment;

Protection of camera lenses from scratching or other degradations that could adversely affect photo quality (especially at micro- and micron-scales);

Software applications to facilitate a detailed ocular examination (including pupil examination) by providers who are untrained or minimally trained in ocular diagnosis;

Overall ease of use by minimally trained personnel; and

Access to appropriate instructional material and software.

As an example of a smartphone, an Apple iPhone or Android-based smartphone (or tablet) can be utilized. In the following disclosure, an iPhone 4S (and iPhone 5S) is illustrated without limitation of generality, and is referred to as iPhone. In addition, features presented with respect to iOS can be applied, without limitation of generality, to Android-based or other operating systems.

The iPhone includes at least one high-resolution digital camera (e.g., about 8 MP) built into the back facing side of the phone such that a user can monitor what the camera is imaging on the actual phone screen. This enables accurate targeting of areas of interest, such as ocular surfaces (e.g., cornea), structures within (e.g., crystalline lens, fundus), and cavities (e.g., anterior chamber and vitreous cavity). The iPhone also includes a front-facing camera that would allow for self-targeting as it is located on the same side as the phone screen. Furthermore, the iPhone built-in digital cameras have an auto-focusing mechanism that can be manually directed to the areas of interest within the camera image. In addition, the iPhone built-in digital cameras can be used to take still images as well as videos.

Close up, macroscopic, and microscopic imaging of ocular surfaces and structures can be achieved by mounting appropriate lenses onto the iPhone-based digital camera. The lens systems may be attached to a ruggedized (e.g., rubberized according to military specifications) phone casing with an opening where the camera is located and may include the use of a customized lens adapter. The entire method of using lenses and adapters for imaging of ocular structures (both self-examination and examination of a subject by a user) is discussed in U.S. Pat. Nos. 7,481,534 and 7,762,664 (sole inventor: Wolfgang Fink), both of which are hereby incorporated by reference in their entirety. These patents also discuss the use of an eyecup, the use of different light sources (IR to visible to UV) to illuminate or stimulate the target region to be imaged, and the use of polarizing filters and filters for UV, visible, or IR light. In some implementations, an eyecup is not utilized.

The (ruggedized) casing may include a rechargeable or non-rechargeable battery, a solar power supply, or other power-supply (e.g., could be fuel-based in one instantiation), independent from the built-in battery of the iPhone. This power source can power the illumination for the ocular structures, and in case of the ophthalmic slit-lamp application, may also power the slit-lamp subsystem. Alternatively, via a specialized adapter, the iPhone built-in battery may be tapped for supplying power to the external lighting systems.

The construction of a general-purpose ophthalmic/ocular imaging system and bio-microscope are both smartphone-based. In some embodiments, the obtained images can be stored on the iPhone and subsequently analyzed and evaluated on the iPhone itself. In various embodiments, the ocular image data can be processed and evaluated on the smartphone, e.g., by utilizing a built-in graphical processing unit (GPU) or general-purpose graphical processing unit (GGPU). If the onboard analyses and calculations are computationally too demanding, the image data can be outsourced to a server backend for further, in depth analyses. The results of such analyses can be sent back to the iPhone and the user. This would constitute a modality or instantiation of telediagnosis and telemedicine.

Referring to FIG. 5, shown is an example of a smartphone-based (bio-)microscope/ophthalmoscope. Customized adapters with lenses for magnification can be used (see, e.g., U.S. Pat. Nos. 7,481,534 and 7,762,664). The custom lens system can include an illumination assembly comprising one or more diodes. An eyecup with cushion allows for positioning of the lens system in front of the subject's eye, while blocking outside light sources. The casing of the smartphone can be threaded to allow for attachment of the lens system. For example, the casing can include a threaded opening that aligns with the built-in camera to allow the lens system to be attached. In other implementations, snap on, magnetic, or other appropriate attachment systems may be used. In some embodiments, a power source (e.g., battery) can be attached to the bottom of the casing to provide power for the illumination assembly. The image of the eye (e.g., iris or other ocular structure) captured by the built-in camera can be displayed on the screen in real time to aid in proper positioning of the lens system. One or more images (or a video) of the eye can be captured using the smartphone controls (e.g., buttons).

Figure 6A:
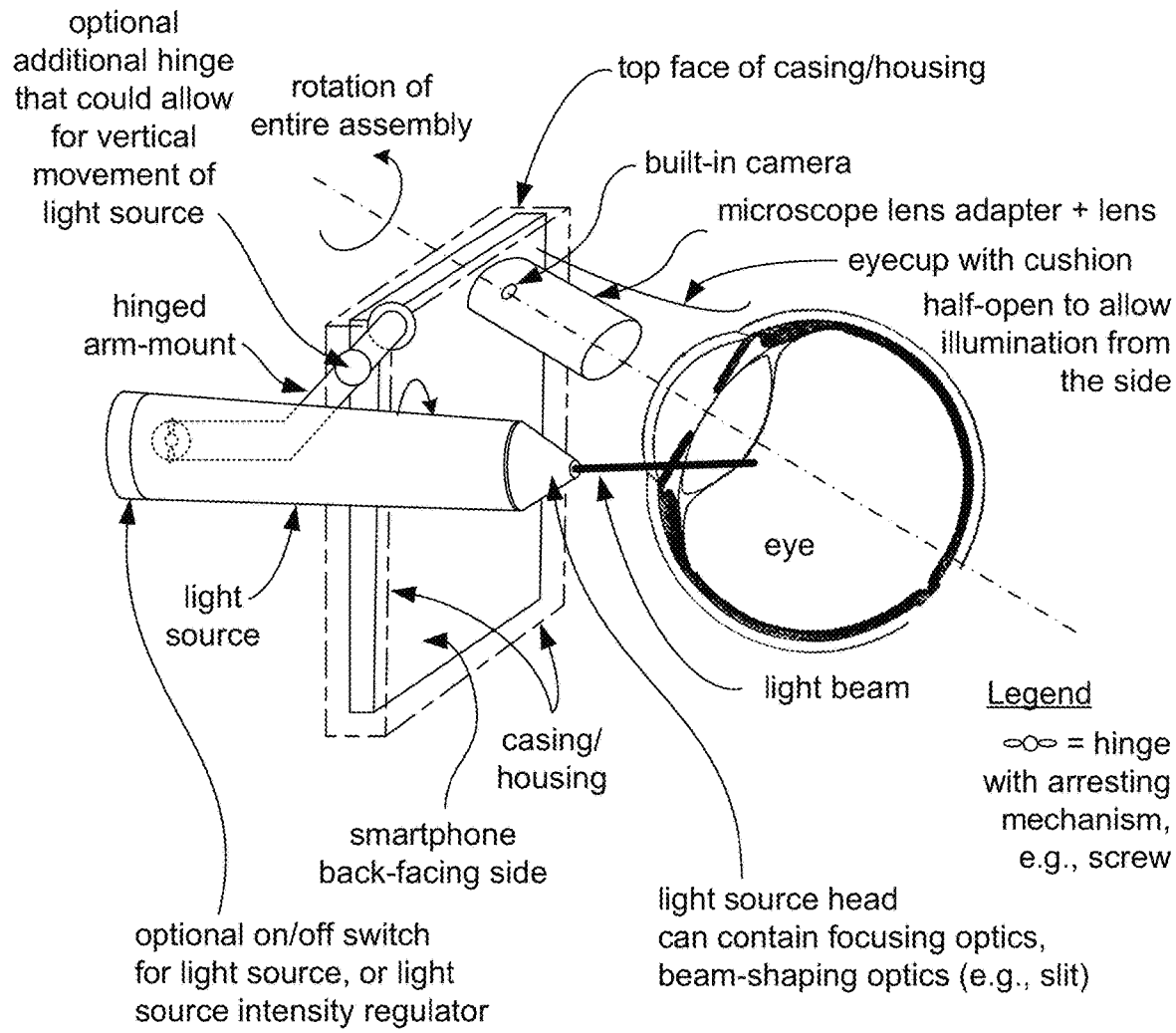
Figure 6C:
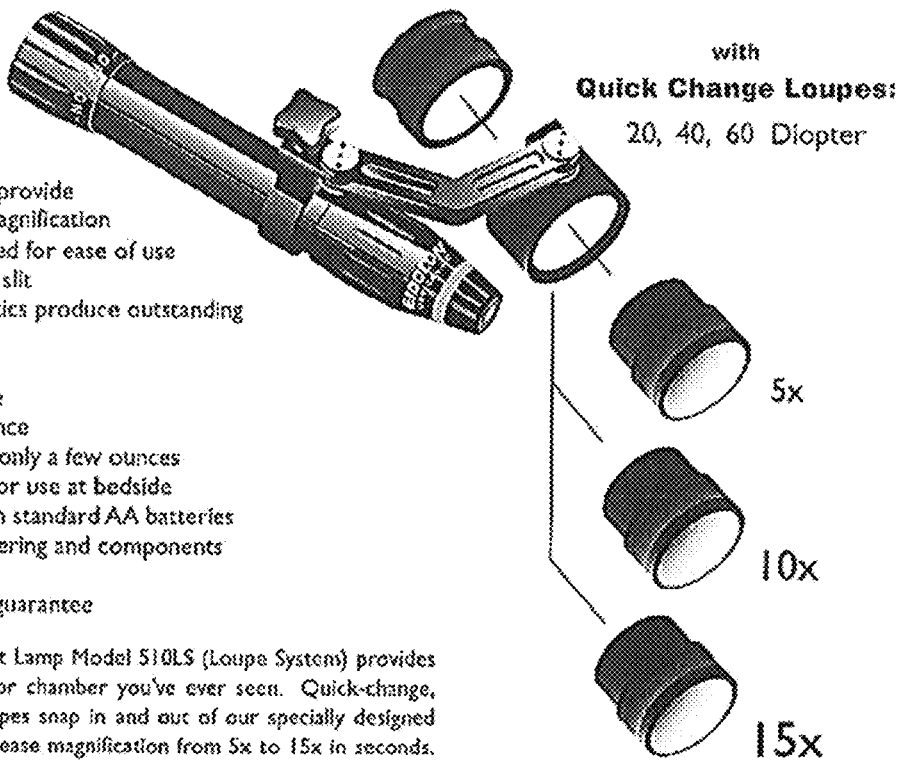
Figure 6D:
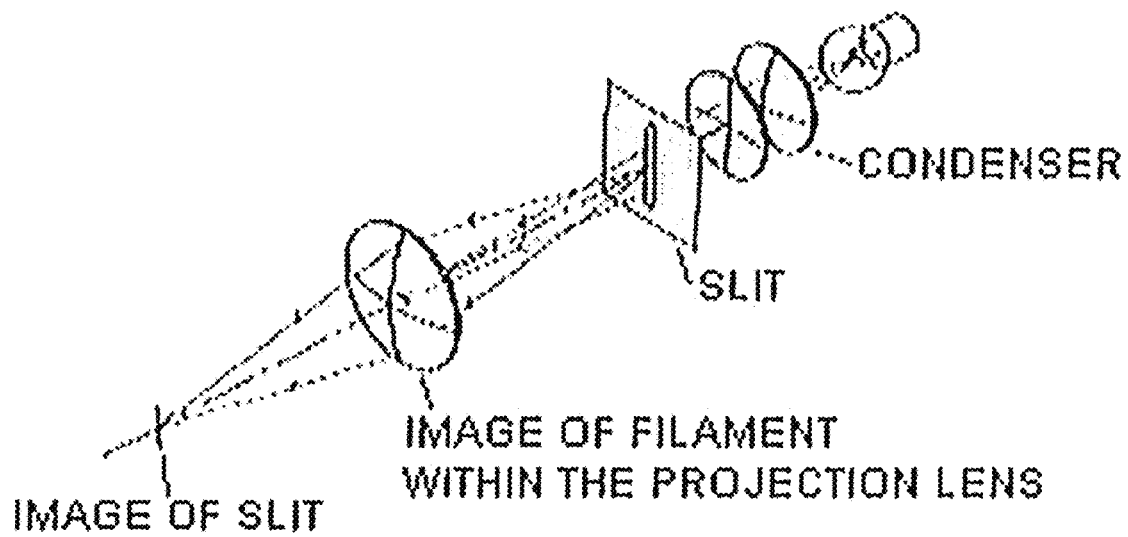

Referring next to FIGS. 6A through 6E, examples of a smartphone-based ophthalmic slit lamp are illustrated. FIG. 6A shows an example of the orientation of the various components of the device. FIGS. 6B and 6C show examples of commercially available handheld slit lamps. The example of FIG. 6A includes a custom lens system with a microscope lens, and an eyecup with cushion can be attached to the smartphone as shown. A portion of the eyecup can be removed to provide an opening for illumination of the eye from the side, which can be provided by a light source secured to the casing of the smartphone. In some cases, an eyecup may not be included. The light source can include focusing and beam-shaping optics, as well as a power source (e.g., battery) to power the light source. FIG. 6D shows an example of the beam-shaping optics that may be located within the light source. The optical component/lens and screen assembly is configured to project an image of a slit of certain dimensions, which may be adjusted (e.g., manually).

As shown in FIG. 6A, a hinged arm-mount can be used to allow for adjustment of the light source position, and thus illumination of the eye. The arm-mount can be located in the horizontal plane of the top face of the casing, to allow the light source to swing forward and to turn inwards to illuminate the eye. In some implementations, arm-mount segments can be length adjustable. Note that the entire smartphone/light source assembly can be rotated and/or translocated by the user with respect to the eye.

Figure 6E:
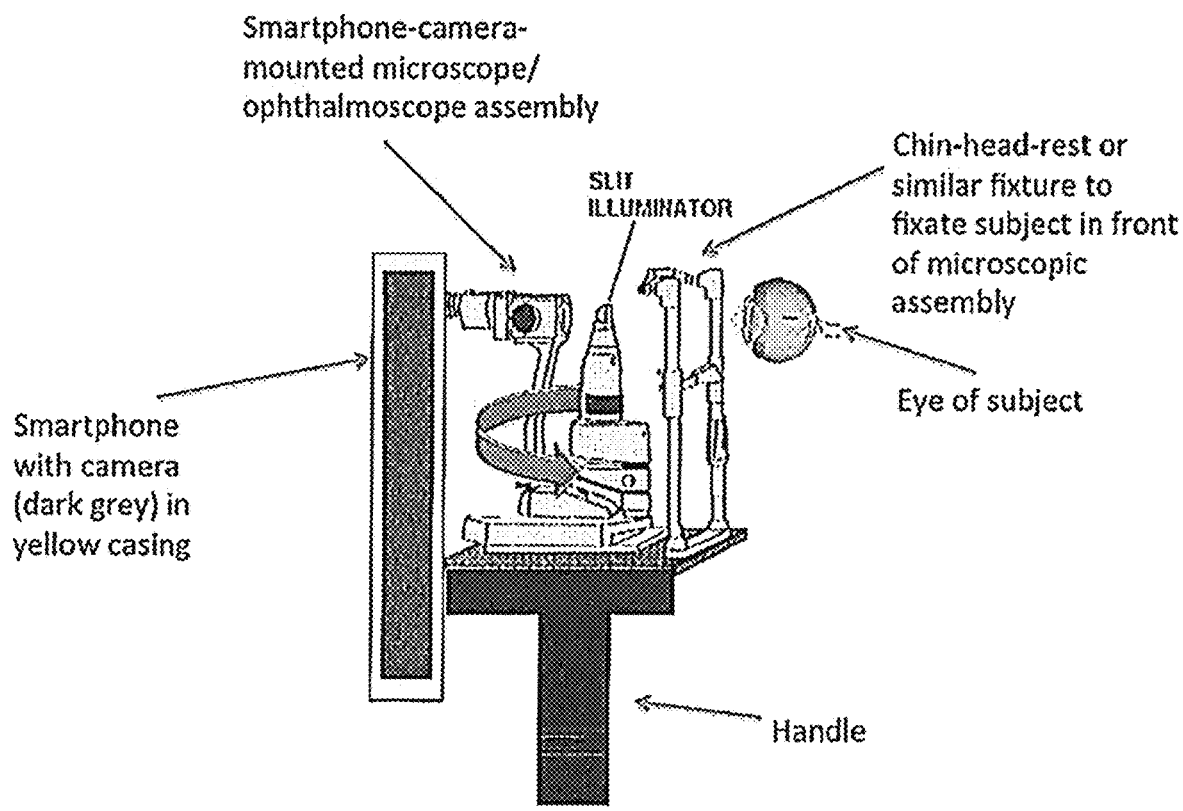

FIG. 6E illustrates another embodiment of a smartphone-based ophthalmic slit lamp. In the example of FIG. 6E, the smartphone casing is coupled to a microscope/ophthalmoscope assembly such that the built-in camera is aligned with the optics. A chin-head-rest or similar fixture can be used to fixate the subject in front of optical assembly. A slit illuminator is included to illuminate the eye of the subject. The hand held, smartphone-based (ophthalmic) slit lamp can be supported by one hand of the operator holding a handle. The other hand of the operator can rotate the attached smartphone around the slit illuminator to image the eye from various angles.

An example of a smartphone-based pupillometer can include illumination diodes inside the eyecup. Note that the partner eye needs to be also covered at the same time because of consensual pupil reaction. Regarding illumination modalities inside eyecups (e.g., light diodes) see, e.g., U.S. Pat. Nos. 7,481,534 and 7,762,664, both of which are hereby incorporated by reference in their entirety. In one embodiment, two different types of light diodes can be used: (a) near IR diodes can illuminate the eye under examination without causing a pupillary reaction, but bright enough for the CMOS or CCD chip of the smartphone-based camera to pick up the image of the pupil (note that CMOS and CCD cameras can be sensitive enough in the near-IR to image the eye or the IR filter can be removed); (b) visible (e.g., white, red, green, blue) light diodes can issue a stimulus to the eye under examination to examine pupillary (reflex) behavior after stimulation such as pupillary constriction time, pupillary redilation time, pupillary capture behavior, etc. With just the near IR diodes it would be possible to monitor (i.e., photograph and/or videorecord) the pupillary dark behavior (also synonymously referred to as "pupillary dark reflex", "pupillary dark response", or "pupillary dark reaction"), such as oscillations.

Figure 7:
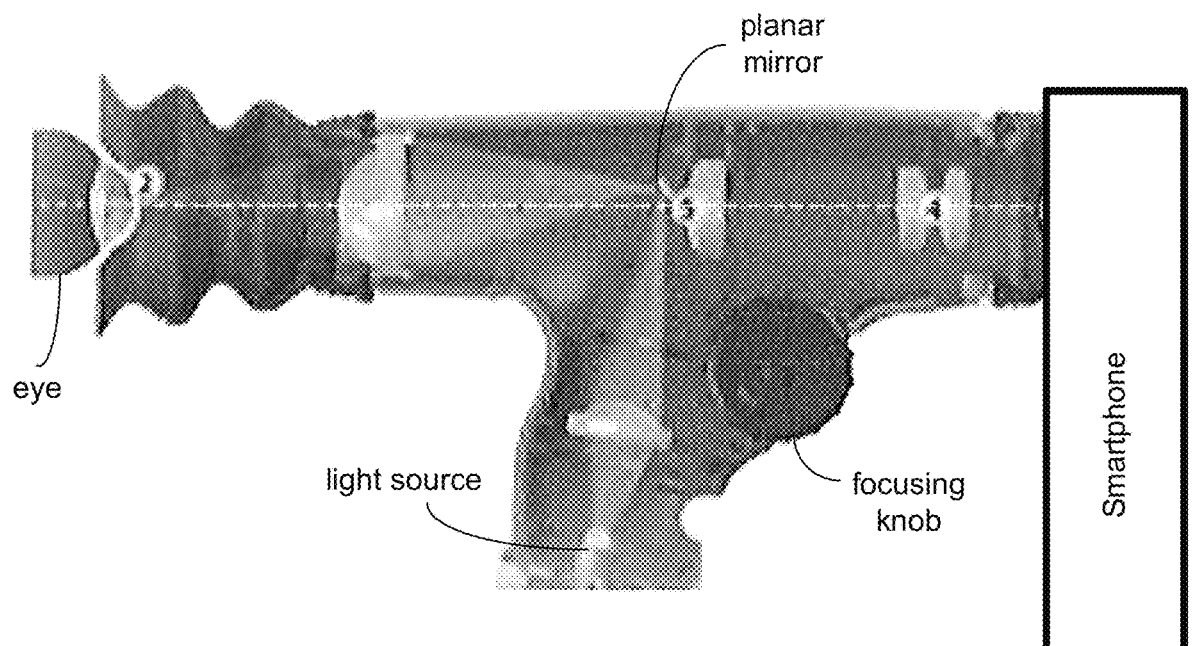
FIG. 7 illustrates an example of a smartphone-based fundoscope according to various embodiments of the present disclosure.

Referring next to FIG. 7, shown is a cross-sectional view illustrating an example of a smartphone-based fundoscope. In one embodiment, the optical component/lens, illumination, and manual focusing assembly depicted in FIG. 7 can be employed as a lens assembly. The fundoscope would be positioned over the eye opposite the smartphone. In some implementations, an optical component/lens, illumination, and manual focusing assembly (round black wheel) enables fundus imaging without mydriasis (i.e., dilation of the pupil). A small planar mirror can be used for rerouting the light from the light source to illuminate the eye. The mirror is placed off-center from the optical axis depicted with a dashed line to not disturb the imaging of the eye.

Figure 8:
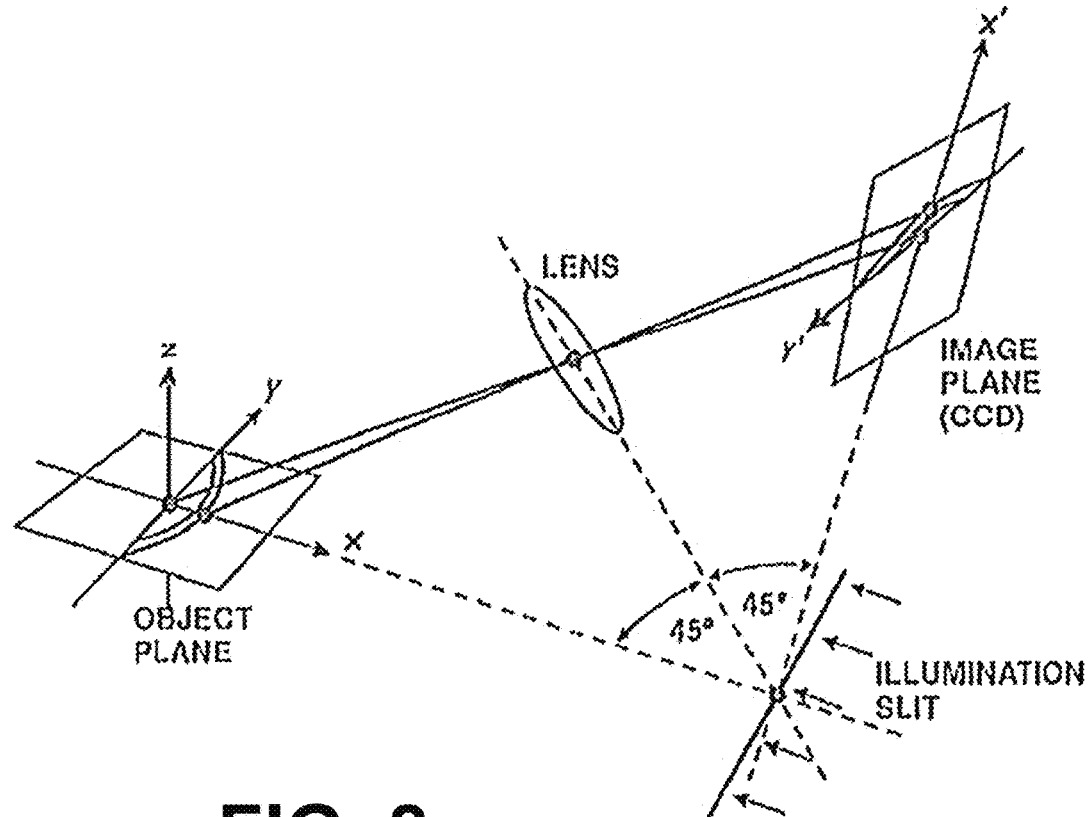
FIG. 8 illustrates a schematic example of Scheimpflug-imaging that can be used by a smartphone-based camera according to various embodiments of the present disclosure.

A smartphone-based Scheimpflug camera uses a similar setup as described for the smartphone-based ophthalmic slit lamp of FIGS. 6A-6E. FIG. 8 shows an example of an illumination scheme for the Scheimpflug-imaging that can be used with the camera. In one embodiment, the illumination setup of FIG. 8 can enable Scheimpflug-imaging of the eye with a smartphone-based ophthalmic device. The "image plane (CCD)" represents the smartphone-based built-in camera, the "lens" represents the (microscope) lens assembly, and the "object plane" is the interior of the eye to be imaged. The imaging optics can be similar, but not limited to, the optics described for the microscope/ophthalmoscope device of FIG. 5 and U.S. Pat. Nos. 7,481,534 and 7,762,664, both of which are hereby incorporated by reference in their entirety.

A smartphone-based stereo imaging device can also be implemented. The stereo imaging capability can be accomplished in several different ways. One basic method would be to take an image from a current smartphone position with respect to the object, e.g., ocular structure or surface, followed by a slight lateral displacement or tilting of the smartphone-based camera, with a subsequent section image of the same object taken. Via onboard (i.e., onboard the smartphone) registration algorithms, or via a server-backend post-processing, range data and a stereo-image (e.g., red blue 3D images) can be generated.

If movement of the smartphone-camera is not a possibility or not desired, one of, but not limited to, the following ways illustrated in FIGS. 9A-9F (and others) can be employed to construct a smartphone-based stereo-photo (macro) or stereo-photo microscope system. Note, in some of the following descriptions only one image is taken to record a stereo-pair of images at the same time, in other cases two subsequent images are taken of the object to be imaged (e.g., ocular structure or surface). In some cases post-processing image correction is utilized, the algorithms for which are known in the literature.

The use of a stereo camera may be implemented using two image sensors (cameras) side by side on a smartphone (see, e.g., "Mirror and Prism Methods for 3d Macro Photography" at http://www.lhup.edu/~dsimanek/3d/stereo/3dgallery16.htm, which is hereby incorporated by reference in its entirety).

Figure 9A:
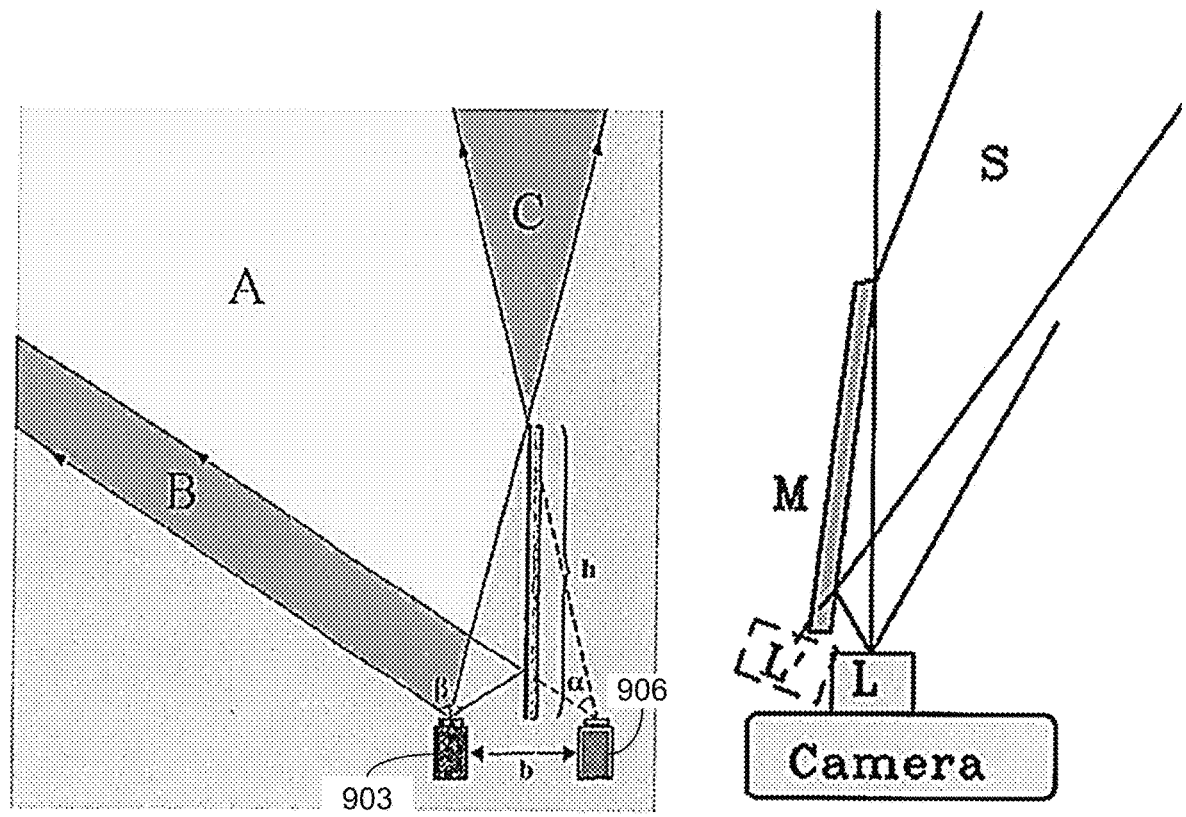

Referring to FIG. 9A, shown is a schematic diagram illustrating a first stereo imaging embodiment. In the example of FIG. 9A, "The diagram to the left shows the principle. The real 2d camera is shown as 903, its mirror image (virtual camera) is shown as 906. These "two" cameras are separated by distance (b). The film or image sensor sees the subject on one side, its mirror image on the other side. The mirror image is reversed right to left and must be transposed later. Both images record the region (A), while the regions (B) and (C) are also recorded, but not in stereo, and this portion of the recorded picture is later cropped away and wasted. The horizontal angle of stereo coverage is considerably reduced. Larger mirror length (h) gives larger horizontal angle and/or allows larger stereo baseline (b). Wth digital cameras we have the luxury of post-processing, so the mirror can be tilted as in the figure at the right, and the keystone distortion rectified later with, e.g., Stereo Photo Maker software. So we can waste less of the sensor area. This is especially useful with small-baseline macro stereo. In the diagram (above right) S is the subject being photographed, M is the mirror, L is the camera lens, L' is the image of the camera lens in the mirror. The trick is to place the mirror nearly perpendicular to the lens axis, tilted inward just a bit, so that the image of its far edge is near the center of the camera sensor. This works best if the camera lens' front element has small diameter. It happens that many digital cameras have small lenses. Here's a case where a wide angle camera lens is an advantage." (Taken from "Mirror and Prism Methods for 3d Macro Photography" at http://www.lhup.edu/~dsimanek/3d/stereo/3dgallery16.htm; © 2008 by Donald Simanek.)

Figure 9B:
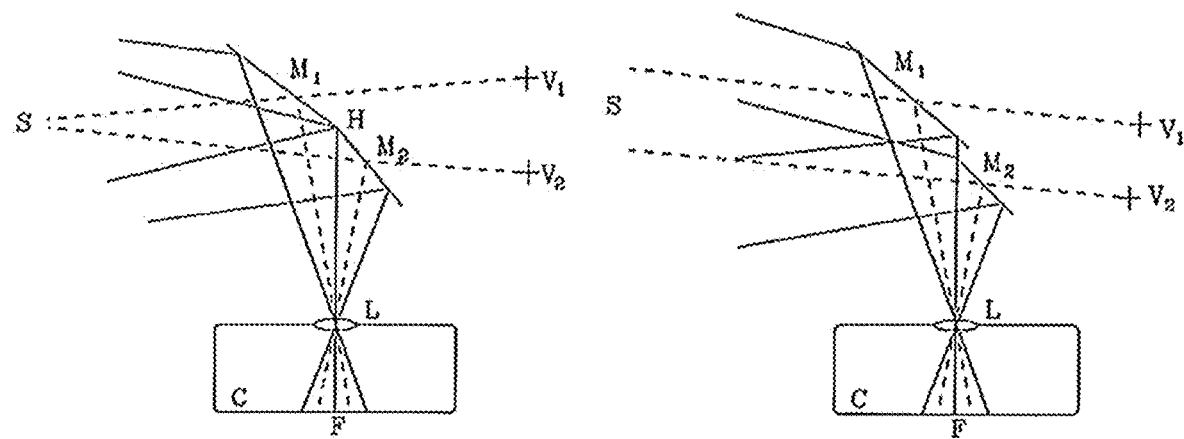
Figure 9B:
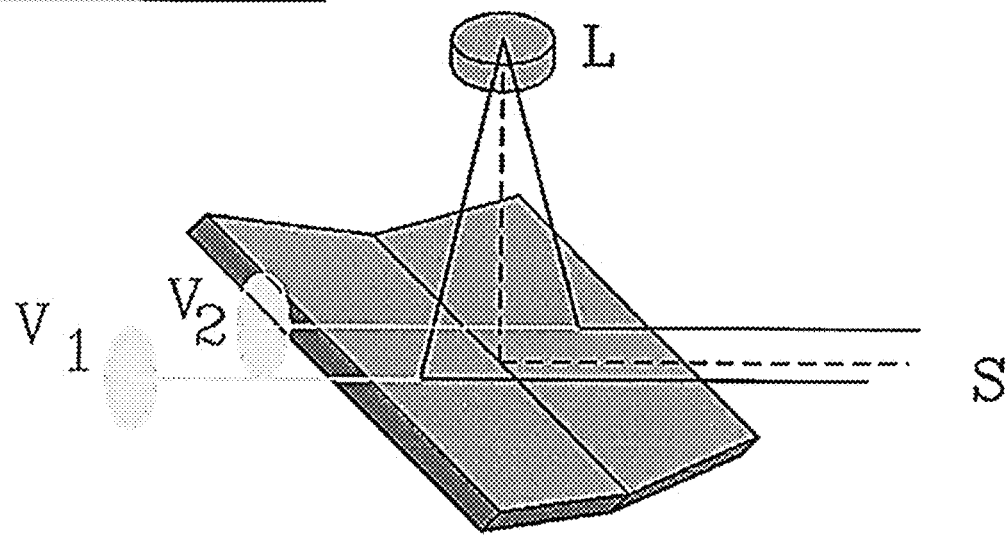

Referring next to FIG. 9B, shown is a schematic diagram illustrating a second stereo imaging embodiment. In the example of FIG. 9B, "Two mirrors $M_1$ and $M_2$ are hinged at H and make a small angle with each other. C is the camera and S is the subject being photographed. The dotted lines in the diagrams show the path of a ray from a centered, subject to the center of its image in the camera. The hinged mirror device creates two "virtual" camera locations ($V_1$ and $V_2$) with displacement and convergence control (left). To control these two variables separately, one can unhinge the mirrors and displace them as shown in the second diagram (right). The mirrors still make a small angle with each other. If they were parallel, the virtual cameras would have diverging line of sight. The mirror angles also need to be adjusted so that the subject to virtual camera distances are equal, and this is why the lines of sight to the subject are both tilted compared to the previous diagram. Similar considerations apply to any device that uses two mirrors with small angle between them. The far edge of $M_2$ defines the dividing line between the L and R images on the film or sensor." (Taken from "Mirror and Prism Methods for 3d Macro Photography" at http://www.lhup.edu/~dsimanek/3d/stereo/3dgallery16.htm; © 2008 by Donald Simanek.)

Figure 9C:
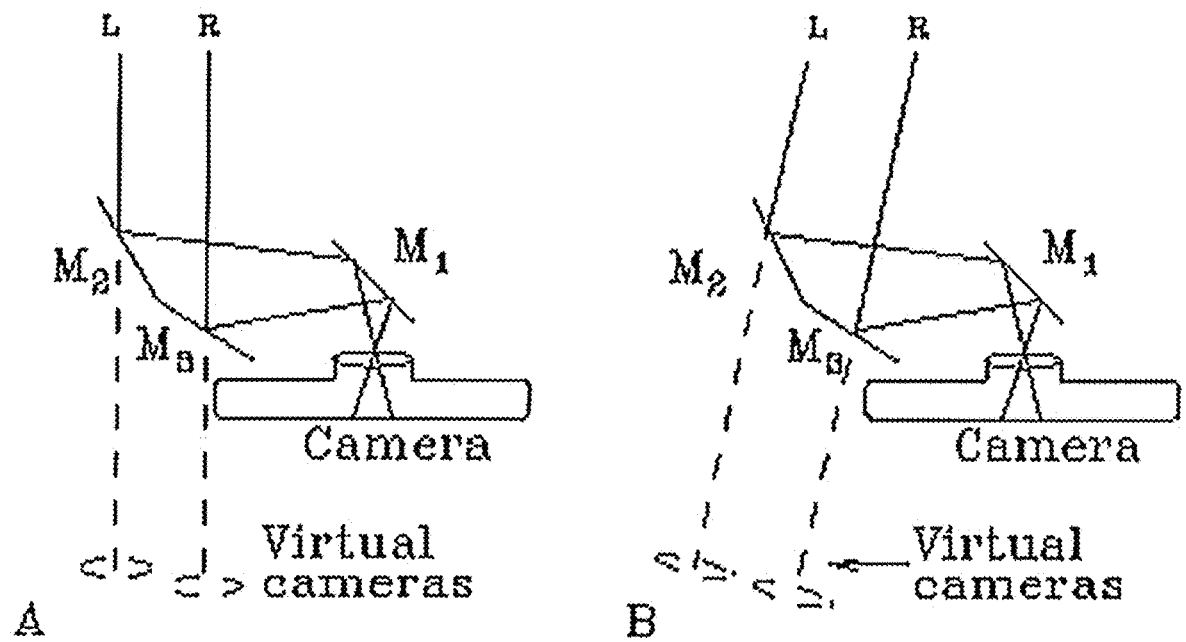

Referring next to FIG. 9C, shown is a schematic diagram illustrating a third stereo imaging embodiment. In the example of FIG. 9C, "The basic idea of creating two virtual cameras with two mirrors at a slight angle can be implemented in many ways. By adding just one more mirror, you can modify the idea to reposition the subject in front of the camera. The figure shows the evolution of the idea. In diagram A two mirrors $M_2$ and $M_3$ make a small angle of 1 or 2 degrees with each other. Mirror $M_1$ is at 45° to the lens axis of the camera, and the other two mirrors are nearly the same angle. The virtual image of the camera lens formed by these two mirrors is shown by the dotted lines. If you draw a scale diagram of this you see a problem right away. The virtual lenses are separated, forming a stereo baseline, but they are at different distances from the subject. The result would be that the L and R stereo images are of different size, and there's a focus disparity as well. The central rays (to the center of each image) from the subject must be of the same length. This can be corrected, as in diagram B by angling the second two mirrors a bit to the right, until the virtual camera lenses lie in the same plane." (Taken from "Mirror and Prism Methods for 3d Macro Photography" at http://www.lhup.edu/~dsimanek/3d/stereo/3dgallery16.htm; © 2008 by Donald Simanek.)

Figure 9D:
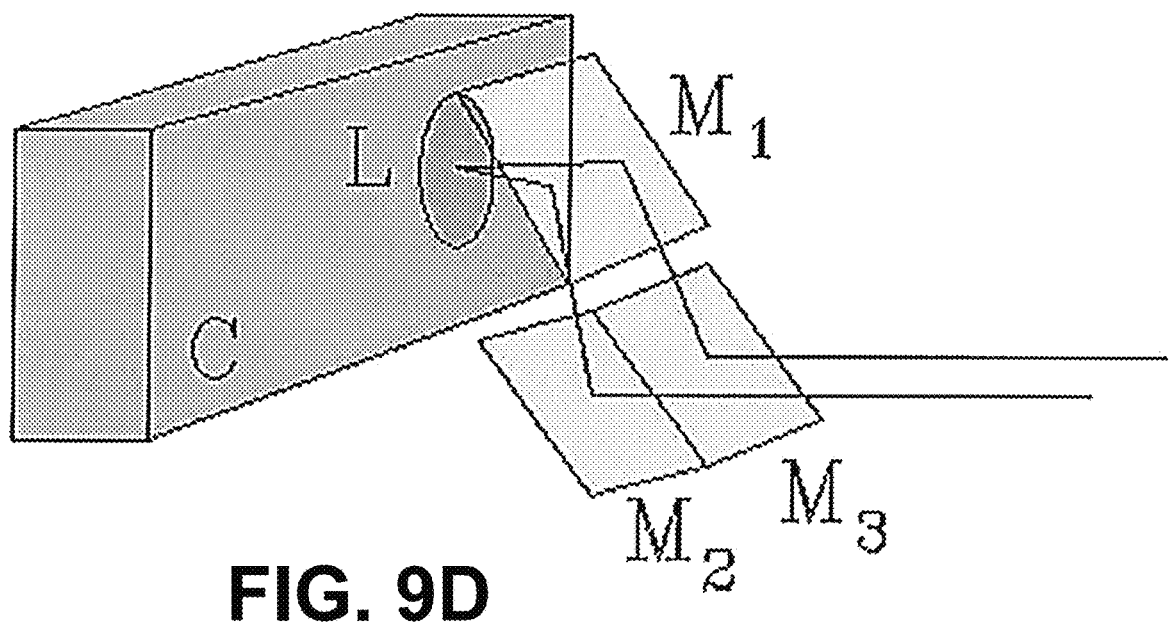

Referring next to FIG. 9D, shown is a schematic diagram illustrating a fourth stereo imaging embodiment. In the example of FIG. 9D, "This assembly is like a two mirror periscope, with one mirror being made up of two mirrors making a small angle. But by placing the angled mirrors below the other one, this arrangement naturally equalizes the two distances from lens to subject, and is easier to adjust. This is just the previous design, but rotated 90°. This system could be used for "normal" 3d photography with a stereo baseline of 2.5 inches and parallel axes. With typical digital "point and shoot" cameras the "wide" lens setting has a horizontal coverage angle of 45°, so each picture of the L/R pair subtends an angle of 22.5°. Now with two mirrors of width 2.5", each at an angle of 5.6° to the camera lens axis (11.25° to each other) the parallel axis condition is achieved. This needs the two mirrors to be 5 inches from the camera lens. That's just barely achievable if you have a camera with protracting lens. Mirror $M_1$ must be small and very near the camera lens. The dividing line between the pictures on the film or sensor is the image of the joint between mirrors $M_2$ and $M_3$. In this system this fuzzy line is likely to be wider at one end. The mirror $M_1$ nearest the lens L is simply a reflector, and may be smaller than the other two mirrors. This system has the advantage that the viewfinder shows the images right side up, and the subject is in front of the camera, where the camera's built in flash (or other light source) can illuminate it. Although we have shown mirror $M_1$ transparent for clarity, all the mirrors are front surface mirrors. For outdoor work, all mirrors should be in an enclosure. The enclosure should also shield the mirrors from the flash lamp." (Taken from "Mirror and Prism Methods for 3d Macro Photography" at http://www.lhup.edu/~dsimanek/3d/stereo/3dgallery16.htm; © 2008 by Donald Simanek.)

Figure 9E:
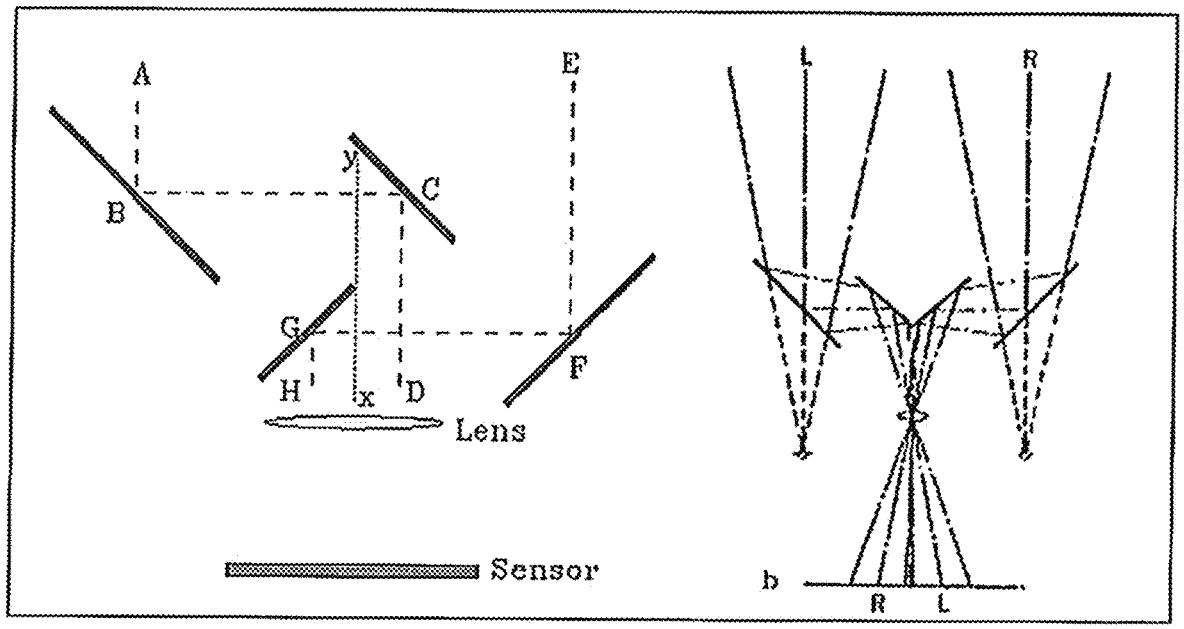

Referring next to FIG. 9E, shown is a schematic diagram illustrating a fifth stereo imaging embodiment. In the left example of FIG. 9E, the diagram shows one possible arrangement (an inverting beam splitter stereo attachment). Mirrors are shown at B, C, F and G. Light takes the path ABCD and passes through a lens (or in some models, two lenses side by side) to form the left eye picture on the right half of the camera sensor. Light takes the path EFGH to form the right eye picture on the left half of the camera sensor. The lens also inverts both images. The dotted line x-y represents the critical location of the edges of two mirrors, which determine the boundary between the two images on the sensor. In particular, the front edge of mirror G is responsible for the location of this boundary, and because it is so close to the lens, it is not sharply defined. This is the reason for the dark boundary between the two images on the sensor, and is an unavoidable feature of all beam splitters of this sort. Spacing must be carefully designed to ensure that the light paths of the central ray for left and right eye are exactly the same length: ABCD=EFGH. (Taken from "The Loreo 3d attachment" Review at http://ww.lhup.edu/~dsimanek/3d/stereo/3dgallery5.htm; by Donald E. Simanek.)

In the right example of FIG. 9E, the diagram shows one possible arrangement (a conventional beam splitter 3d attachment). Many beam-splitter adapters have been marketed that use mirrors or prisms and a single lens and camera. Few are still sold. Their reflective surfaces were arranged as a combination of two periscopes. They put the L and R images side by side on the film frame or sensor, each image taller than wide. The effective horizontal angle of view of the lens is halved. The figure at the right shows how the mirrors form two virtual images of the camera and its lens, their spacing being determined by the front mirror spacing. Sometimes the same adapter, or a similar one, is used with a slide projector and polarizers to project side by side stereo images superimposed on a metallic screen, using linear or circular polarization to separate the images. This design was patented as the "Stereophotoduplicon" in 1894 by Theodore Brown, and described in his book *Stereoscopic Phenomena of Light and Sight*, The Gutenberg Press, Ltd, London 1903. (Taken from "Mirror and Prism Methods for 3d Macro Photography" at http://www.lhup.edu/~dsimanek/3d/stereo/3dgallery16.htm; © 2008 by Donald Simanek.)

Referring next to FIG. 9F, shown is a schematic diagram illustrating a sixth stereo imaging embodiment. In the example of FIG. 9F, "With the single objective 3D microscope system, the operator looks down at the objects imaged by the sensor. Each of the rays 909 represents the center of mass of a cone of light that reaches the sensor as the optical modulator switches between the right- and left-view states. The optical modulator selects different angles for the light rays in each view, creating separate viewpoints within the single lens. Projecting the right-view image to the right eye and left-view image to the left eye creates a stereoscopic image." "Consider one technique to capture two images through a single lens. By blocking a portion of the lens, a new center point, closer to the edge of the non-blocked side, is created. If the left half of the lens is blocked and captures an image frame and then the right half of the lens is blocked and captures an image frame, two images from different viewpoints are created—in other words, a stereoscopic image pair." (Taken from "Single-camera, 3D microscopy promises biomedical imaging benefits" by Shawn Veltman and Paul Dempster; May/June, 2012 edition of BioOptics World; see the same article for more detail and references provided therein.)

Z-stacking is also applicable to 3D microscopy. Z-stacking takes multiple views of the same sample with different focus settings to obtain a rough idea of 3D space. Post-processing of the images is utilized for this.

Applications that are envisioned include, but are not limited to, glaucoma testing via fundoscopy, fundoscopy/fundus camera, pupillometry, macro- and micro-imaging of ocular surfaces and interior structures, slit lamp, Scheimpflug imaging, hyperspectral imaging, and/or stereo imaging of the eye, telediagnosis via server backend, and/or in-situ diagnosis via the smartphone. Different smartphone-based ophthalmic devices can be envisioned by combining these components.

Referring now to FIGS. 10A and 10B, shown are examples of a smartphone-server backend interaction for bidirectional data transfer between an iPhone and a server backend for fully automated telediagnosis. Initially, the server establishes a global presence on a known IP address and port. The server creates a background thread to wait on incoming requests. As depicted in FIG. 10A, the following steps can then be repeated as needed:

The iPhone user selects an image from the photo library, or takes a snapshot with the built-in camera, or records a video.

The iPhone instantiates a TCP/IP connection over the internet with the server.

The iPhone submits the image/video data to the server in native graphical format (PNG, PPM, JPG, etc.) or movie format (e.g., MPEG-4 (mp4)).

The server receives and validates the image/video to be processed/analyzed.

The server runs custom analysis program on the image/video.

The server generates end data products (e.g., modified/processed image/video, analytic data, diagnoses, etc.).

In some implementations, another user (e.g., physician, expert) looks at the iPhone-delivered data on the server and analyzes them manually and/or by engaging other tools to generate end data products (e.g., modified/processed image/video, analytic data, diagnoses, etc.) on the server.

The server returns the modified/processed image/video and/or analytic data products to the requesting iPhone.

The server drops TCP/IP connection to the iPhone while maintaining the incoming request port.

The iPhone receives and displays the modified/processed image/video and/or analytic data products to the user.

What is currently lacking in modern telemedicine is the capability of in-situ, near real-time analysis and diagnosis of the image data obtained with such smartphone-based ophthalmic examination devices. For example, some iPhone apps can take, store, and retrieve fundus images on the iPhone, however they are completely devoid of any kind of analysis—therefore useless from a telemedicine point of view. In contrast, to establish a true smart service platform, a server-based telediagnostic analysis capability can be provided for the smartphone-based ophthalmic examination devices.

Such a server-based telediagnostic analysis capability can utilize a "Smartphone-to-Server Backend Interaction for Bidirectional Data Transfer" as illustrated in FIG. 10B, which can be described as follows:

Standalone server process framework;

Server method for establishing a global 24/7 online presence on the Internet;

Method by which the server process is able to receive inbound requests;

Protocol for remote interfacing to a smartphone frontend application;

Multithreaded capability to enable processing of simultaneous multiple requests originating from several smartphones;

Procedure to invoke algorithm for detailed analysis of the raw input data;

Capability for processing input image/video data and production of a modified version of the input;

Delivery capability to return the results of analysis processing to the smartphone frontend; and/or Archival database system for all requests.

The smartphone-communication framework is the backend to the opthalmological interface that the user can run on a smartphone. It can collect unprocessed opthalmological image/video data and can supply this data to the server back end for specialized analysis processing. The results of the analysis can be displayed onscreen. For example, the smartphone-communication framework can comprise the following functional elements:

Method for the smartphone application to acquire unprocessed opthalmological imagery and/or video data from the device's built-in camera on demand;

Protocol by which the smartphone application communicates to the server process back end;

Capability of packing/encoding the acquired raw image data into network-streamable packets fit for sending over the Internet to the server process back end;

Reception capability for retrieval of the analysis results over the Internet from the server process back end; and/or Method for relaying the analyzed/processed data to the smartphone's ophthalmic imaging application.

An example of an implemented smartphone-based handheld ophthalmic examination device will now be discussed. A handheld ophthalmic device to image the pupil of the eyes in order to analyze the current medical state of a subject was designed. Monitoring and collecting the diameter of the pupil through three different modules will achieve this. Module one comprises monitoring the pupillary reactions of both eyes with a short light stimulus stimulating only one eye. Module two comprises monitoring the pupillary reactions of both eyes with a prolonged light stimulus stimulating only one eye. The short light stimulus can be defined to be about hundredths of a second and the prolonged light stimulus can be defined to be about 20 seconds. Module three comprises monitoring pupillary reactions of both eyes without a light stimulus or in total darkness. In order to detect the current medical state of a subject, data, such as the pupil diameter, can be recorded as a function of time, plotted in real time, and then analyzed and interpreted. Medical conditions such as drug use, state of fatigue, and recognition of diseases can be detected through conducting these three tests. A swinging flashlight test can also be automated and performed using a pupillometer to detect, e.g., efferent and afferent lesions to the brain.

The overall system includes placing the device (smartphone attached to headgear) onto the subject's head followed by stimulating the subject's eye. The iPhone will then capture a video of the eye through the activation of an app. The data collected can then be sent to an external server; the server will then process the data and send it back to the iPhone for real time plotting/rendering, or, alternatively, the iPhone will receive a data plot, for example in form of a picture (e.g., JPG, etc.). In both cases, a professional can interpret the data.

System characteristics can be divided into four sections: functional, non-functional, technology, and performance. Functional characteristics can include, but are not limited to:

The ability to monitor a pupil in complete darkness while the subject is in bright daylight;

The ability to monitor the pupillary diameter of one or both eyes as a function of time in the presence of a light stimulus;

The ability to perform a real time evaluation of the pupillary diameter in one or both eyes in complete darkness;

The ability to send a light stimulus to one eye;

Full user control over time and lighting constraints;

The ability to easily switch from one eye to the other eye;

The ability to export data and results for analysis on external systems; and

The ability to calculate and make available the following information: maximum and minimum pupillary diameters, re-dilation time, light stimulus latency time, and constriction time.

Non-functional characteristics can include, but are not limited to, a user manual and handbook on how to operate the device, minimal effort to transition between examinations or eyes, and no need for an external tool to transition to a new test. Technology characteristics can include, but are not limited to, a mobile device, battery powered, hardware modification including the removal of the camera's IR filters, implemented using mobile platform (e.g., Apple iOS mobile platform), smartphone hardware platform (e.g., iPhone 6 or iPhone 5S), cleaning and sanitizing before each use should not put the device at risk of damage, and cloud computation can be implemented for image processing and data handling. Performance characteristics can include, but are not limited to:

Minimum of 60 Hz resolution;

Sampling frequency of 120 Hz;

Minimum resolution of 1280×720;

Perform multiple modalities (e.g., pupillary light reflex, pupillary capture, and pupillary escape);

Capture latency time;

Maximize pupil resolution; and

Image processing at near real time via an external server.

A peripheral camera may be used in case usage of device camera is an absolute drawback to meeting requirements. Auxiliary hardware may be used in case use of device hardware renders meeting requirements impossible. The weights and dimensions of the device should not exceed the average weight of a motorcycle helmet or football helmet.

Because the handheld ophthalmic device involves applying a light stimulus to the eye, safety regulations are considered and reviewed during installation, testing, and maintenance. The human eye is very sensitive and over exposure to IR, lasers with high intensity beams, or exposure to light over long periods of time can yield retinal damage, cataracts, or photo keratitis (inflammation of the cornea).

Retinal damage occurs between the wavelengths of 400 to 1400 nanometers and occurs when radiation is transmitted through other areas of the eye to the retina. The trauma level is dependent on the exposure time and amount of radiation absorbed. People who experience retinal damage usually experience mild problems such as headaches, short-term blindness, or photophobia.

Cataracts can be described as an accumulation of protein over a period of time that creates a film in the lens of the eye preventing a patient from seeing clearly. Cataracts can be developed from many medical conditions such as diabetes or drugs, but can also develop from radiation or light exposure. Clouding of the eye usually occurs between 315 and 400 nanometers. People with cataracts usually experience cloudy vision, double vision, a change in the way they see certain colors, and more. This condition can be treated with glasses and or surgery.

Photo keratitis can be described as inflammation of the cornea. This condition usually occurs between 180 and 315 nanometers. People with keratitis usually experience pain, blurry vision, and are sensitive to light. Keratitis can be treated with antibiotics or prescribed eye drops. Keratitis can be prevented by limiting exposure to radiation and avoiding eye injury.

For example, four IR light-emitting diodes (two per eye) can be used for the imaging module for the camera with a wavelength of 860 nm. The IR illumination allows for imaging in total darkness without stimulating a pupillary light reflex. For the light stimulator module we will use, e.g., 2 white LEDs (one per eye). As mentioned before, the LEDs will be on for a short period of time (e.g., fractions of a second), or a prolonged period of time (e.g., 20 seconds). Each LED contributes a quarter of the total radian flux, with an intensity set to approximately 121-µW radiant flux.

The smartphone-based handheld ophthalmic examination device includes three subsystems: mechanical, optical, and electrical, all of which have their own design concepts. Each of these subsystems will be described separately.

There are four considerations that apply to the mechanical sub-system: have the ability to monitor a pupil in complete darkness while the subject is in bright daylight, have the ability to send a light stimulus to one eye, cleaning and sanitizing before each use should not put the device at risk of damage, and the device should be mobile. These functions can be accomplished by: making the headset opaque and making sure it fits snuggly to the subjects head, creating an eye divider that will fit snuggly to each eye socket, creating separate holdings for the optical and electrical components that are water tight, and making sure the device is compact enough to not cause harm to the subject's head or neck.

The design for the headpiece can be a completely 3-D printed piece. There are four major subsystems in this design: holding areas for the optics, electronics, each eye compartment, and the iPhone. Each piece can be designed and printed separately. Both the optical and electrical holdings can be hollow and have doors that provide easy access to those components, each eye can be incased separately so that only one eye will be stimulated at a time, and there can be a holder on the front of the goggles that the iPhone can snap in and out of quickly. There may also be a head strap that will be affixed to the goggles to keep them sitting comfortably, and tightly, to the subject's face.

Figure 11:
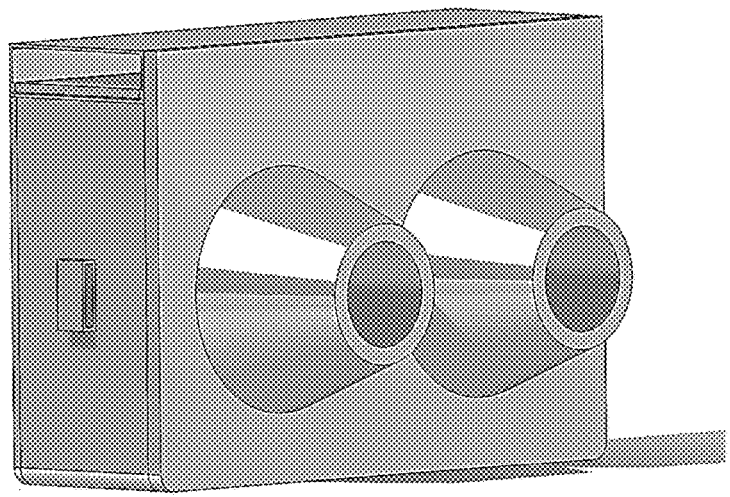
FIG. 11 is a graphical representation of an example of goggles that can be used in a smartphone-based ophthalmic examination device according to various embodiments of the present disclosure.

Referring to FIG. 11, shown is a graphical representation of an example of goggles that can be used in the smartphone-based ophthalmic examination devices. A mockup of the 3-D printed model was created using SolidWorks. FIG. 11 shows the eye dividers that can be pressed against the subject's face to separate the eyes. The small open rectangle on top can hold the electronics for the device, and the larger rectangle that runs length-wise (pictured here with the holder for the head strap attached) can house optical components. Foam can be placed on the rims of the two eye divider cones for comfort and to keep light out. The optical component holder dimensions, the large vertical rectangle in FIG. 11, drive the overall headpiece measurements. The electrical component holder, the small horizontal rectangle in FIG. 11, can hold the various electrical components as well as the wires for the LEDs. A goggle-based design including optical and electrical components positioned at the front offers various advantages in cost, material, and labor.

Four conditions were considered for the optical system in one instantiation: this system allows the image capture or filming of both eyes simultaneously, will comprise a cube beam splitter, and/or mirror, and/or prism assembly to capture both eyes, be compact to maintain overall system portability, and allow for filming of the eyes without light present. These conditions can be met by: using a cube beam splitter to allow for the filming of both eyes simultaneously, using components that are only a cubic inch in volume, using IR LEDs to allow for filming in darkness, and choosing a beam splitter and right angle prism that operate in total darkness.

Figure 12:
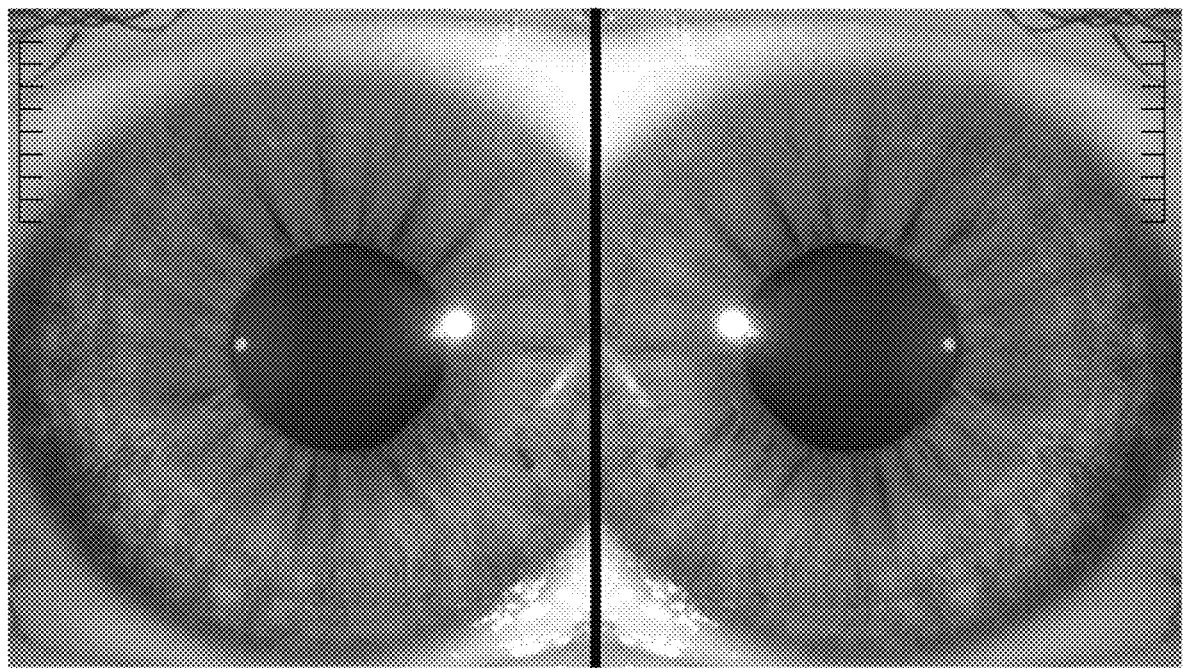
FIG. 12 is an example of simultaneously captured images of both eyes of a subject according to various embodiments of the present disclosure.

A cube beam splitter (e.g., 25 mm 50:50 Cube beam splitter, 750-1100 nm) can be placed in front of one eye with a right angle prism mirror (e.g., 750-1100 nm) placed in front of the other eye. Light can transmit directly through the beam splitter from the eye that the beam splitter is placed in front of, and the eye placed in front of the right angle prism will have its light reflected to the beam splitter cube. These two rays will recombine upon entry into the beam splitter and be transmitted directly to the camera of the smartphone (or tablet) where both light from both eyes will be waiting to be captured or filmed. FIG. 12 shows an example of an image that simultaneously captures both eyes of the subject. A reticle can be included to accurately determine dimensions and/or size of parts or aspects of the eye.

In the example of FIG. 11, there are two major subsystems: the optical component system and the illumination system. The optical system includes the right angle prism mirror and beam splitter cube as previously discussed, but can also include collimated lenses to be placed in front of these components as well. The illumination system can include two (or more), e.g., white LEDs for inducing stimuli into the test subject's eyes, and can also use four 860 nm IR LEDs for illumination and filming in total darkness.

Figure 13A:
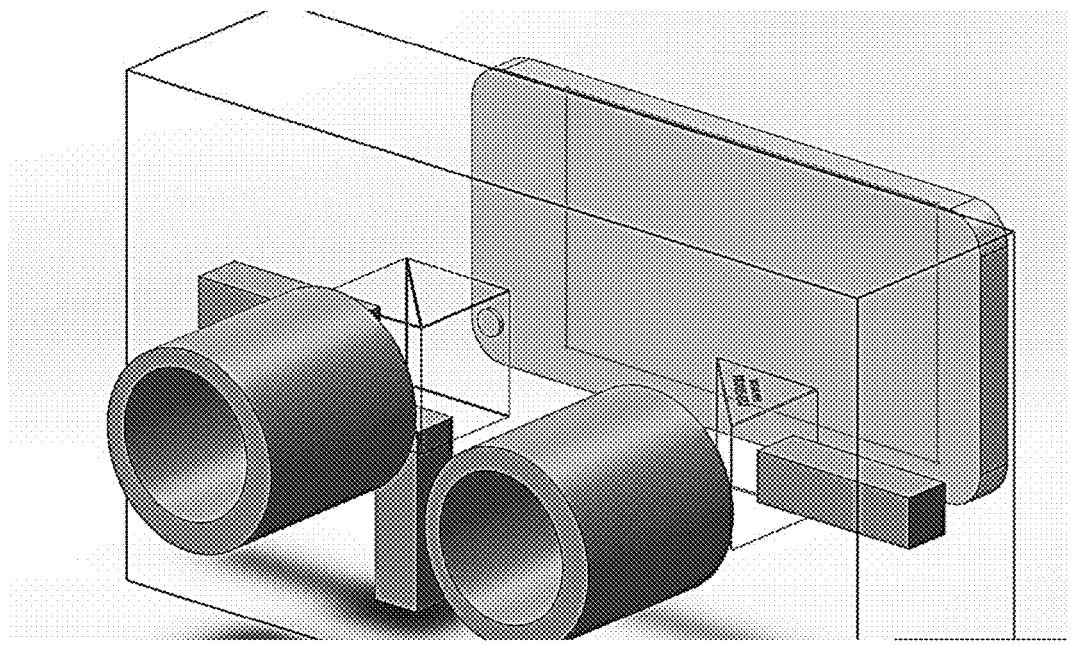
FIGS. 13A through 13C illustrate an example of an optical system design of a pupillometer according to various embodiments of the present disclosure.
Figure 13B:
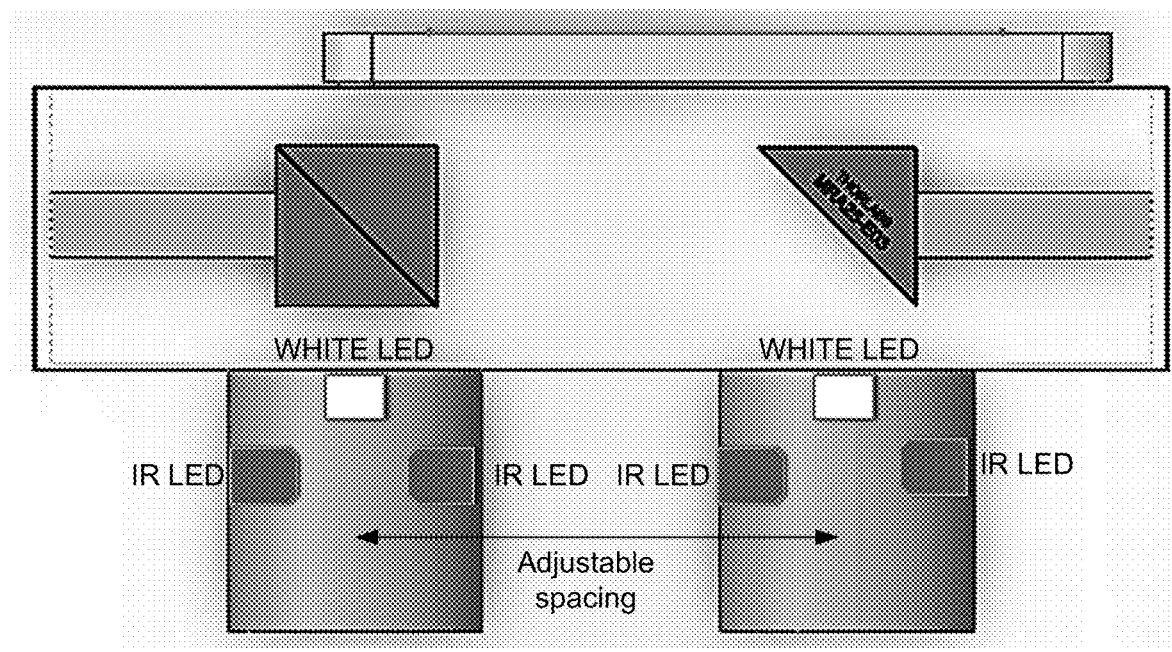
Figure 13C:
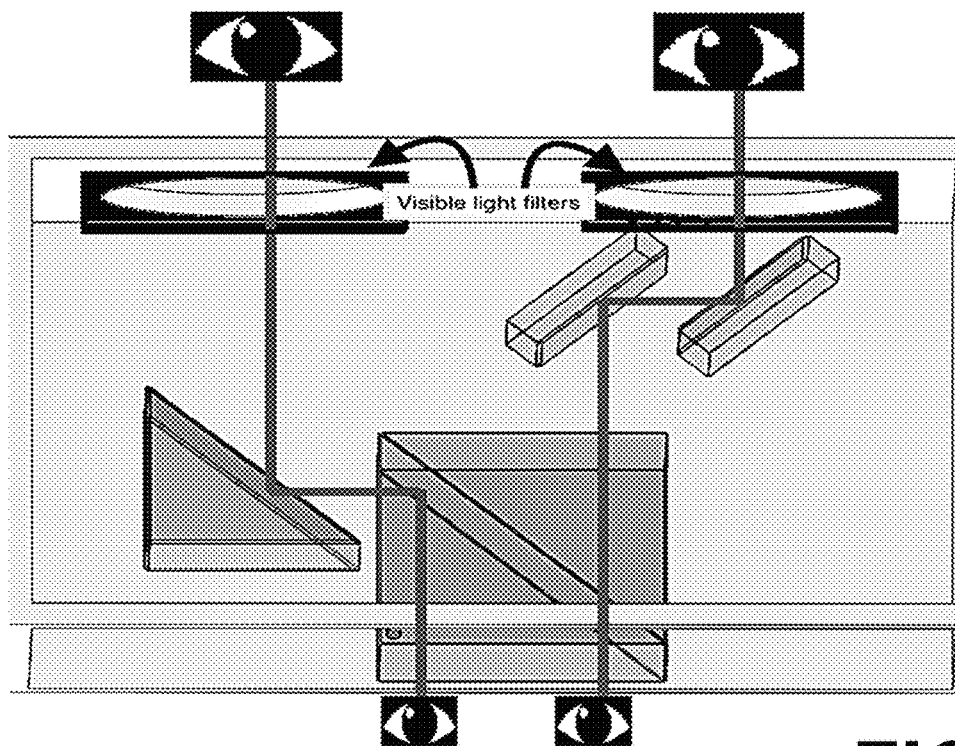

FIGS. 13A through 13C illustrate an example of an optical system design of a pupillometer, showing iPhone orientation, eye separation compartments and beam splitter. The optical system includes a beam splitter cube in front of one eye, a right angle prism mirror in front of the other eye, most likely being mounted on a translation stage to account for people who have eyes that are spaced apart differently, as well as collimation lenses placed in front of each of these components. The translation stage allows for adjustment in spacing between the eye pieces as illustrated in FIG. 13B. It was found that use of a right-angle prism mirror offered advantages over a simple flat mirror. While slightly heavier, the right-angle prism mirror was easier to mount and align. Size and alignment are important considerations for the optical system, which makes the right-angle prism mirror a better option. A beam splitter cube or a semitransparent mirror may be utilized to combine light from the eyes before sending it to the camera. The beam splitter cube offers notable advantages in alignment and mounting.

For the iOS Software, four conditions were considered: capture using the built-in device (iPhone), use of the iOS platform, obtaining photo and videos captured with 1280× 720 resolution, and graphing of the final result. These conditions can be met by: using the built in iPhone 5s camera, using for example the iOS platform, using for example the iOS AV Foundation Framework, and using for example the Core Plot Charting Library.

Figure 14:
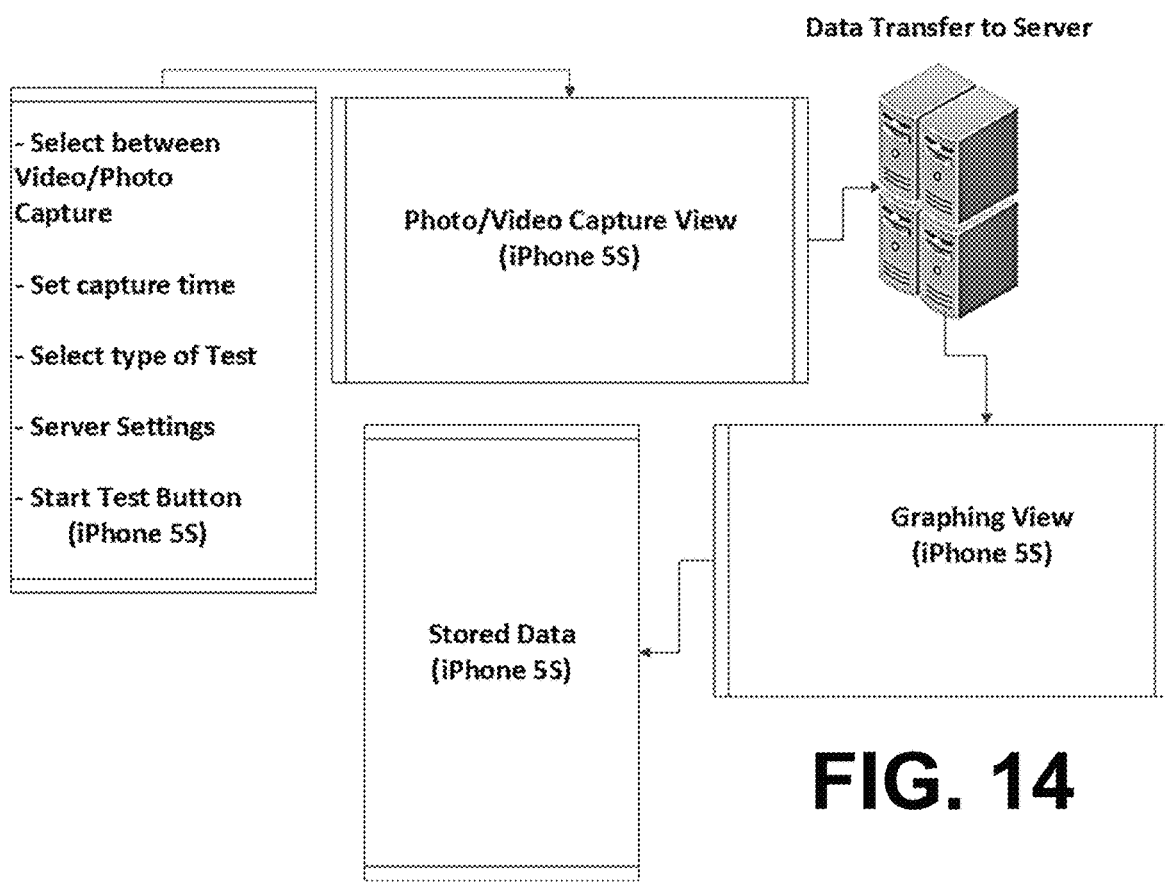
FIG. 14 is a flow chart illustrating an example of smartphone application interactions with a server according to various embodiments of the present disclosure.

Referring next to FIG. 14, shown is a flow chart illustrating an example of functionality of a smartphone application (e.g., iOS app). As it can be seen in the Flowchart of FIG. 14, the iOS app can have four major views, each with specific tasks. The first view of the app can be responsible for providing the user the capabilities of selecting what type of capture to perform (either photo or video) select duration of test as well as information pertaining to the address of the remote server. The second view can show the capture operation in real time. After capture, the data can be sent to the remote server for computation. Next, the smartphone receives the computed result from the remote server, graphs the final output and provides the option of storing the final result on the phone. One aspect of the iOS app will be the ability to shoot videos or photos for a specified length of time. The photos or video captured can then be transferred to a remote server for computation. The user may have the option of selecting what type of capture to be performed (video or photo capture) as well as specifying the length of time for the capture.

In order to meet the condition for capture, the iOS AV Foundation Framework can be implemented in the app. This is a framework, or collection of programming files with instructions and specifications on how to manipulate and program audiovisual programs on the iOS platform. While color images offer advantages for the other ophthalmic applications, for best results with the pupillometer the capture can be done in gray scale. In order to meet this performance condition, the OpenCV Library, which is a programming library used for computer vision programming, can be used for example.

The file transfer can take place between the smartphone (or tablet) and the remote server. After a given capture, the smartphone transmits the files to a remote server. After computation, the iOS app downloads the result from the server. For example, the file upload will follow the following steps:

A write stream can be created by the iOS app for data upload; and

The captured data can then be uploaded to the server by sending the file in small increments, following an iterative process, until the whole file is uploaded.

Similarly, the download process will be as follows:

First the iOS app will check if there is a file ready for download;

A read stream will be created for data download; and

The iOS app will download the file from the server in small increments, iteratively, until the entire file is downloaded.

The file transfer portion of the iOS app can also handle download and upload errors. Whenever an upload or download is not successful, the iOs app may notify the user about the error. For example, the CFNetwork Framework, which contains a set of TCP/IP protocols, can be implemented in order to meet the conditions for uploading and downloading files.

Figure 20:
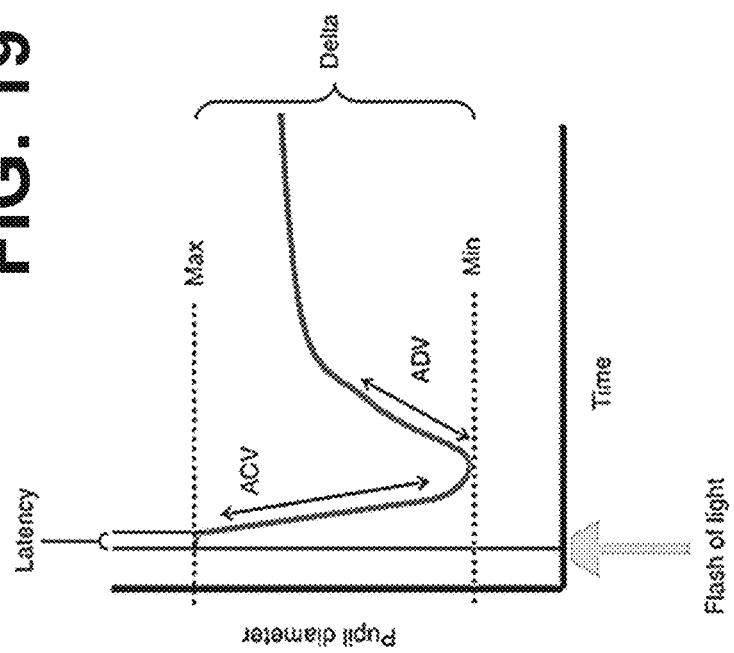
FIG. 20 illustrates pupillogram metrics measured by the server back-end system of FIG. 19 according to various embodiments of the present disclosure.

The iOS app, after receiving computed results from the server, can plot a graph of pupillary diameter variations as a function of time. In order to achieve this, a Core Plot Charting Library can be implemented for example. This library can permit plotting of a 2D graph as a final output result. FIG. 15A shows an example of a graph obtained by using the Core Plot Library. FIG. 15B shows an example of pupillary diameter variation over time. FIG. 20 provides additional details for pupillogram metrics that can be measured. FIG. 16 depicts an example illustrating operation of the iOS software (or app).

Figure 17:
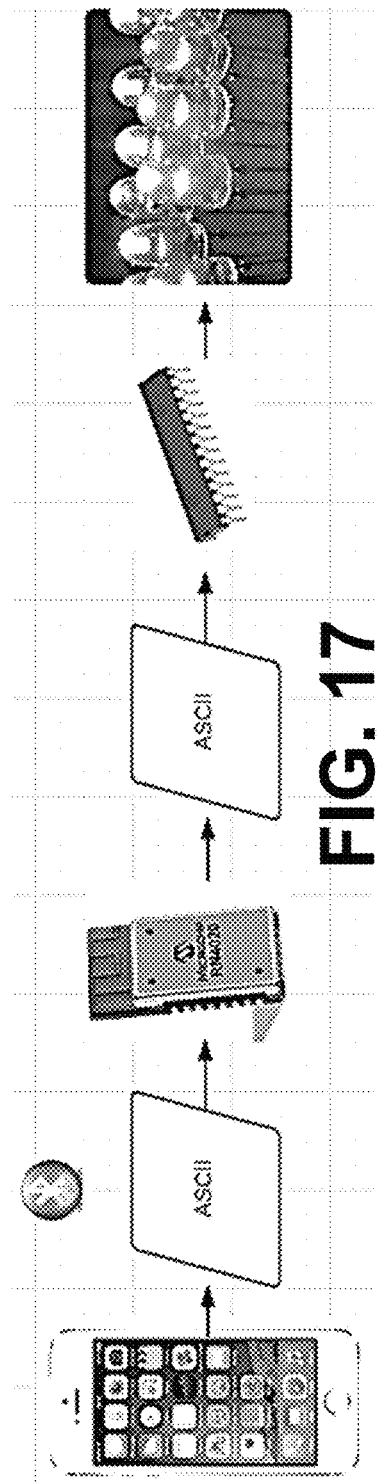

For the electronics, the following conditions were considered: the ability to send a light stimulus to one eye; full control over time and lighting constraints by the user, and a battery powered device. These conditions can be met by: coding the microcontroller to only allow one eye's LEDs to illuminate at a time, programming the microcontroller to analyze, e.g., ASCII sent from the iPhone and determining user specifications, and using a power source such as a 9V battery. FIG. 17 shows a flow chart illustrating an example of the electronics. As it can be seen from FIG. 17, that user specifications can be sent, e.g., as an ASCII (message or code) via Bluetooth. A low energy module chip can receive the ASCII and relay it to a microcontroller that it is hardwired to. The microcontroller can then interpret the ASCII and command the lighting system to function according to the user specified settings.

Figure 18A:
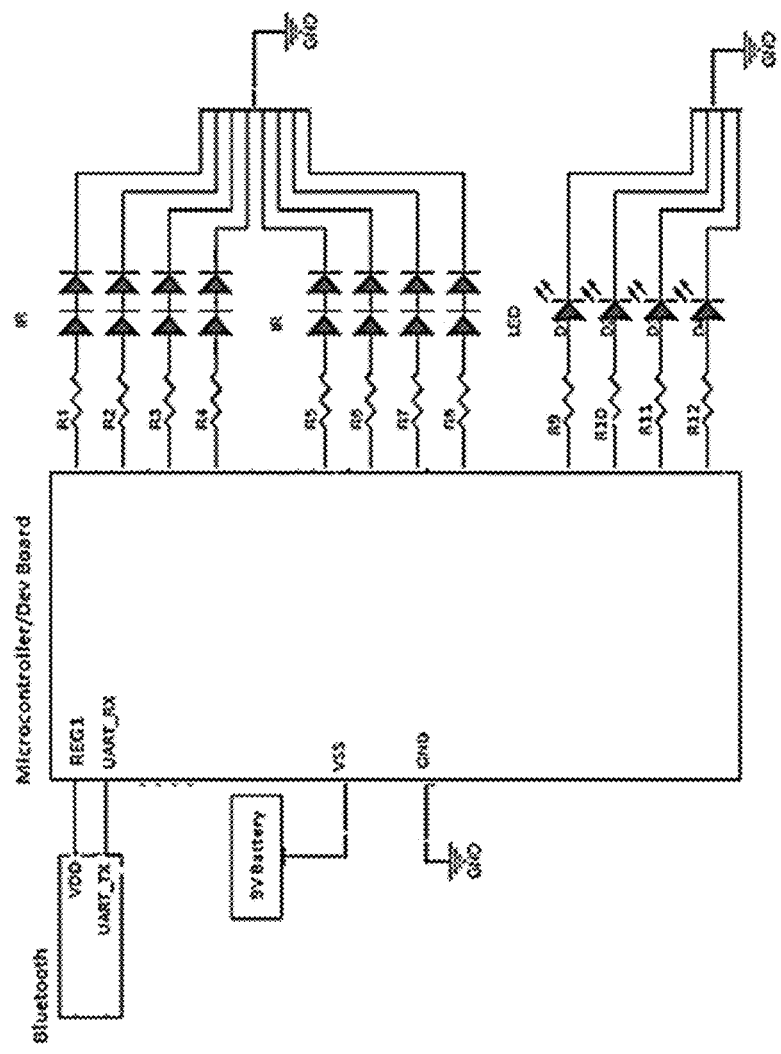

Referring to FIGS. 18A and 18B, shown are schematic diagrams illustrating an example of the circuitry. In the example of FIGS. 18A and 18B, it can be seen how the electronics components will be connected to each other. For instance, a 9V battery can be wired directly to a board (e.g., ICP23—Iboard Tiny X28 (Circuit Technologies) microchip 28-pin development board), which the microcontroller (e.g., PIC16LF1938-E/SP (Microchip Direct) 28-Pin Flash-Based 8-Bit CMOS MCU) is attached to. The board can include, e.g., a voltage step down which can step down the 9V to the 3.3V that the microcontroller needs to function. That same 3.3V can also supply the power needed for the Bluetooth module (e.g., RN4020 (Circuit Technologies) Bluetooth Low Energy Module) or other wireless communication module to function. The Bluetooth chip and the microcontroller can be hardwired through their UART pins, the Bluetooth will transmit, and the microcontroller will receive. In one embodiment, eight infrared LEDs along with 2-4 white-light LEDs can be attached to the I/O pins. According to the microcontroller datasheet, the maximum current through any I/O pin is 25 mA, which is capable of supplying the 20 mA needed to ideally, illuminate each LED. In FIG. 18B, it can be seen which pins of the microcontroller will be used for each component. However, the LED pins have not been indicated. Other implementations are possible as can be understood.

For the interaction between the iPhone and the microcontroller, Bluetooth was chosen over Wi-Fi due to user convenience. It was felt that perhaps a user would find it inconvenient to have to login to a Wi-Fi network before each operation. In addition, the only benefit with Wi-Fi would be its ability to transmit and receive at further distances than Bluetooth. However, since the iPhone and microcontroller will be in close proximity, this advantage was not applicable. In other embodiments, Wi-Fi can be used.

For the server backend system, two conditions were considered: calculate the biometric data (e.g., minimum and maximum pupil diameter, re-dilation time, reaction latency, and constriction time), and cloud computation of image processing. These conditions can be met by: the reception and extraction of TCP/IP transmissions containing image data from an iOS client, image processing based upon examination and eye characteristics, software utilization of C/UNIX/OpenCV/MPI, calculation of examinations metrics, and building and transmitting the analysis and/or graph data file (as an ASCII.dat for example).

Figure 19:
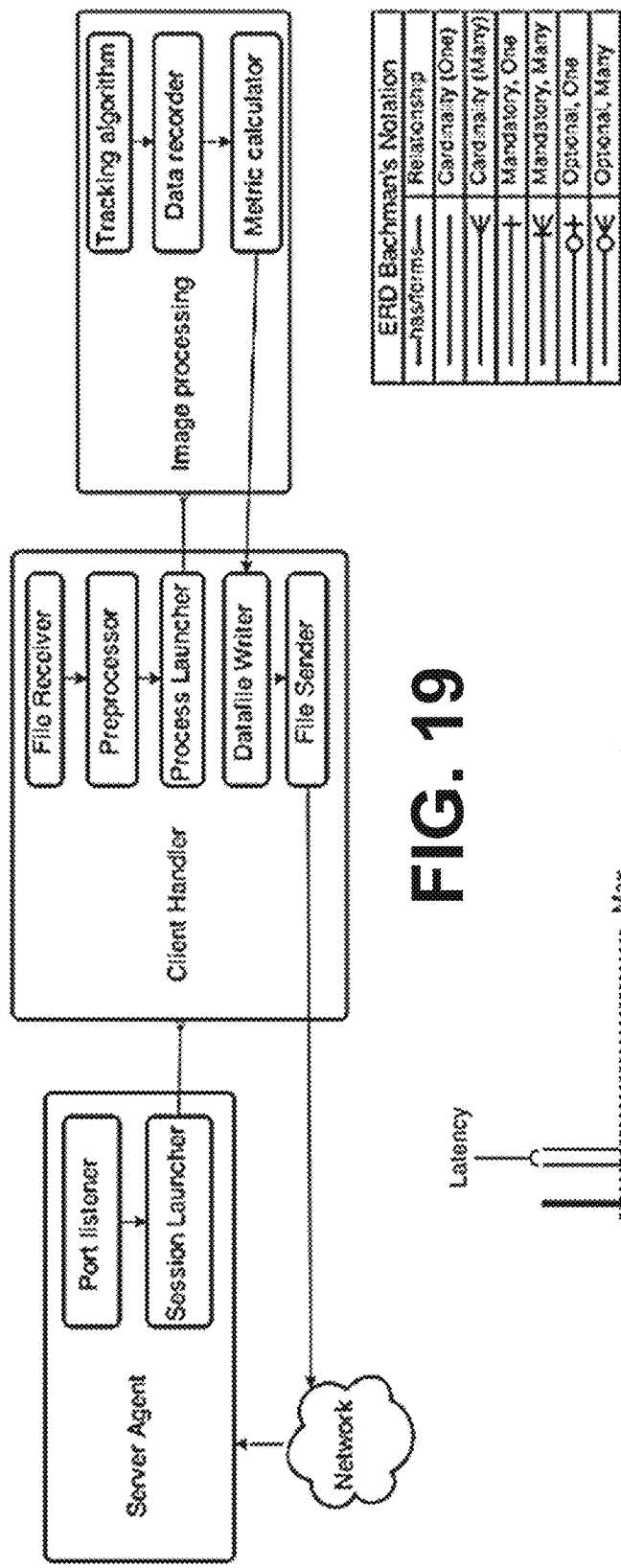
FIG. 19 is a flow chart illustrating functionality of a server backend system according to various embodiments of the present disclosure.

FIG. 19 shows a flow chart illustrating functionality of the server backend system. The example of FIG. 19 is with respect to the pupillometer. However, the same functionality can be used to transmit and process individual images for the other ophthalmic applications. An overview of software processes involved in the server backend system can be seen in FIG. 19. An incoming TCP/IP connection can be opened upon receipt of a request from the iOS client. After opening the port, the video file can be received and preprocessed before launching the processing tasks. After the processing is performed, the appropriate biometric data can be written to the return file and sent over a TCP/IP socket connection back to the iOS client. The software can be written, for example, in C on a Unix-based Operating System. Any errors can be communicated through the deliverable ASCII data file returned to the client.

The Server Agent can be a TCP/IP port listener (e.g., written in C) that monitors for incoming connections on server port 9099. Message Passing Interface (MPI) will be used to facilitate parallel processing throughout the program. Because every frame in a video sequence is identified by a sequence number, the overall video may be easily partitioned and mapped to several processing algorithm routines and organized for concurrency by the Client Handler. When an incoming connection is established, the Server Agent can interpret an initial integer receipt to determine whether the client is requesting a new session or a continuation of an existing session. This is because the socket connections will be terminated after the file receive step and not re-established until the file is ready to send from the server.

Each Client Handler can process runs in its own thread in order to facilitate robust performance in the server system. This means that multiple device clients may process different tests simultaneously, but one implication is that the Server Agent may continue to respond to pings while the image processing is being performed. The primary responsibility of the Client Handler is to check the incoming video file for errors and perform preliminary pre-processing tasks (as applicable) prior to the image processing step. These pre-processing tasks include steps such as Binary Thresholding (partitioning the image pixels using a brightness threshold) and Particle Removal (removal of any artifacts with a diameter below a certain threshold). If multithreading is used to process the video file in parallel, this step can also be performed here. Different and/or additional image processing algorithms can also be applied for the other ophthalmic applications.

After preprocessing is completed, separate threads can then be launched for the Image Processing portion of the program. When the Image Processing routines return, the Client Handler is responsible for writing the data file with biometric data used at the iOS client (or other operating system based client). The data can be written in, e.g., an ASCII.dat file that can be parsed by the iOS client. The biometric calculations that the Client Handler is required to perform are as follows (and are shown in FIG. 20):

Minimum and maximum pupil diameter: In relative calculations (measuring in percentages), this measurement may be somewhat trivial. However, in absolute measurements a scale can be used and the exact pupil diameter (uncorrected in terms of optical distortion from the eye lens) may be estimated.

Constriction time and Re-dilation time: These are estimated by defining the exact frames in which the eye meets a certain size threshold (with respect to maximum/minimum size) and dividing their distance in frames by the known Frames-Per-Second (fps) quantity of, e.g., 60 Hz.

Reaction latency time: This is the time between the initial light stimulus and the pupil reaching or passing below a certain size threshold in response. It is calculated in a method similar to constriction time and re-dilation time.

FIG. 20 is an overview of example metrics measured by the server back-end. Sending of the deliverable ASCII.dat file is performed once a final TCP/IP connection has been established with the client. Until that time, the information is saved on the server for later reference. The TCP/IP socket is finally closed after successful transmission of the file.

The image processing agent is responsible for identifying the segmented pupil circle and measuring the diameter in the present frame. One thread process exists for each video partition created in the preprocessing routine. The data from this task can be written into memory shared with the parent process (in the Client Handler) and concurrency is enforced in the Client Handler. Four algorithms were considered for the image processing steps in this module. All four methods described are considered successful methods for tracking pupil diameter (other methods may be known to the ones skilled in the art):

"Curvature Algorithm"/Least Squares fitting: Traverse around pupil boundary to find edges and fit a rounded line to the pupil. This algorithm claims the ability to find the pupil diameter with less than 40% of its outer edges visible.

Sobel Algorithm (http://en.wikipedia.org/wiki/Sobel_operator): Traverse the image with a 3×3 matrix and determine the directional derivative in all directions for each iteration. This algorithm is included in the OpenCV API. It is regarded as very fast due to its use of bit-shift multiplications of the edge pixel values.

Hough Edge Detection (http://en.wikipedia.org/wiki/Hough_transform): Standard edge detection algorithm for solid circles. This algorithm is included in the OpenCV API. Many optimized libraries exist for the algorithm.

Active Contours, Deformable Models, and Gradient Vector Flow/snake algorithms: such as that described in "Active Contours, Deformable Models, and Gradient Vector Flow" (http://www.iacl.ece.jhu.edu/static/gvf/).

Additional algorithms can be employed for the other ophthalmic applications, e.g., fundus analysis, etc.

Figure 21:
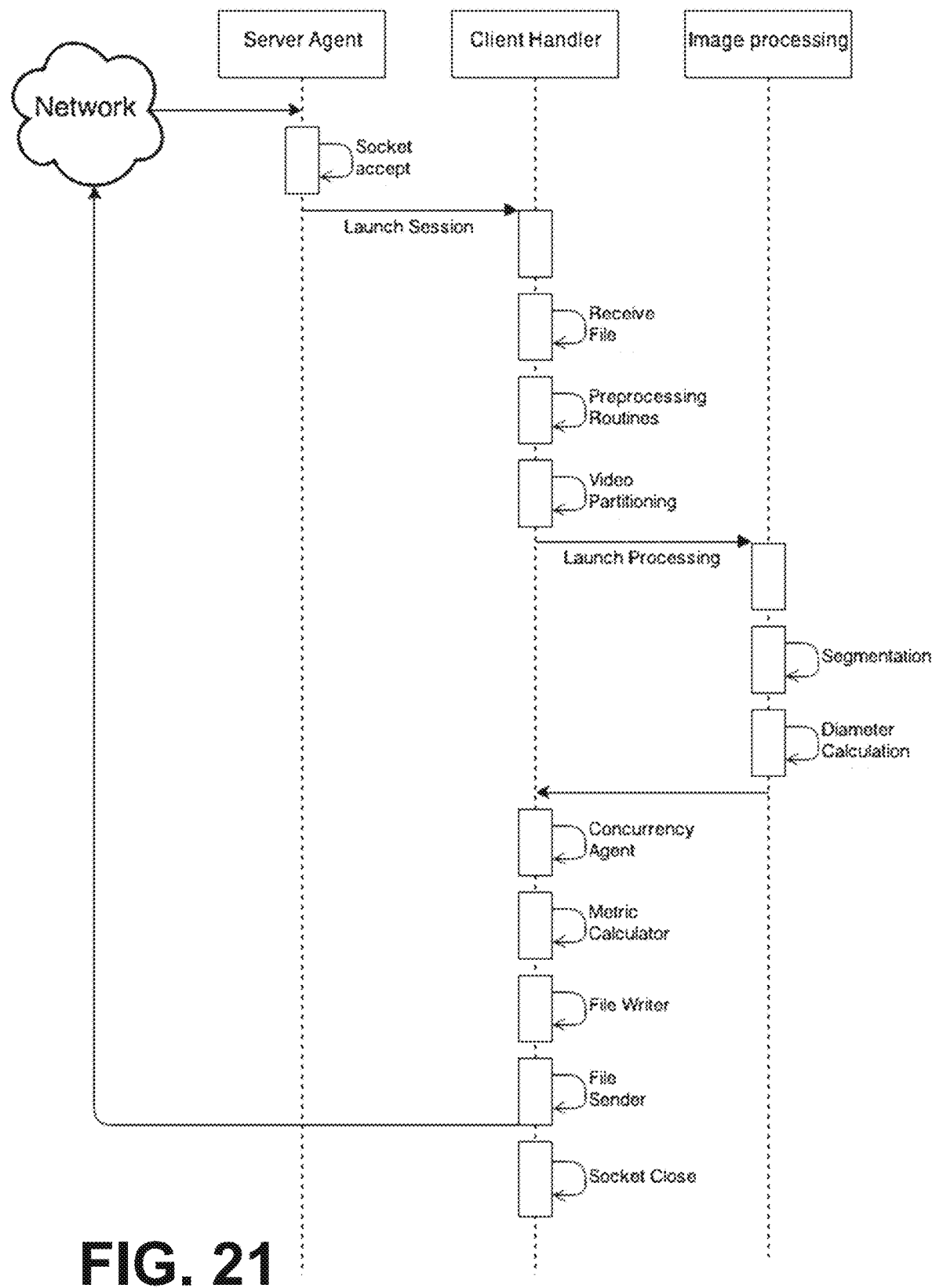
FIG. 21 is a sequence diagram of an example of the ophthalmic examination module interactions according to various embodiments of the present disclosure.

Because of the specific nature of the problem, a "Hough Circles" OpenCV algorithm can be used due to the fact that the optimized library can be readily applied to circle tracking. This program can be compared to Canny (simple) Edge detection. One or more of algorithms may be utilized to provide improved results and/or accuracy. A sequence diagram (or flow chart) of the interaction between these modules can be viewed in FIG. 21.

The mechanical, optical, and various electronic subsystems can be joined seamlessly in order to create a product that fulfills the conditions. The designs described in this disclosure can be implemented, including providing a sample grey scale or color video or images from the smartphone to the server, the Bluetooth communication operations, parsing the iOS data file, and optimizing the LED placement.

Figure 22A:
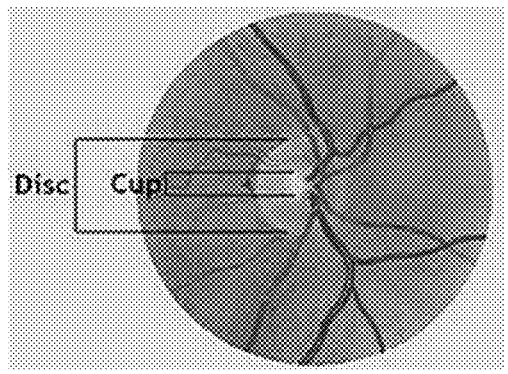
FIGS. 22A through 22D illustrate examples of ophthalmic examination processing according to various embodiments of the present disclosure.
Figure 22B:
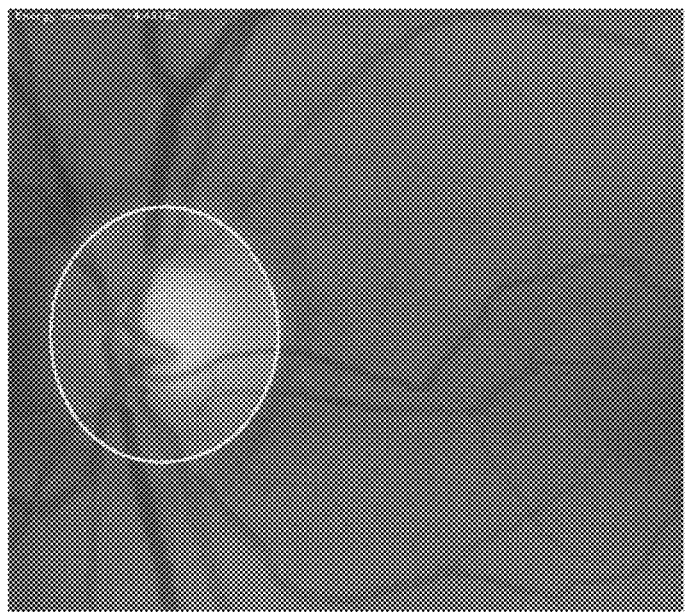

Smartphone ophthalmic imaging application: As another example of an automated and diagnostically useful analysis, consider the early detection of glaucoma, the leading incurable blind-making disease, by calculating the cup-to-disc ratio via image processing. The cup-to-disc ratio is a measurement used in ophthalmology to assess the progression of glaucoma. The optic disc is the anatomical location of the eye's "blind spot", the area where the optic nerve and blood vessels enter the retina. The optic disc can be flat or it can have a certain amount of normal cupping (see, e.g., the cup and disc in a fundus image of FIG. 22A). But glaucoma, which is due to an increase in intra-ocular pressure, produces additional pathological cupping of the optic disc. As glaucoma advances, the cup enlarges until it occupies most of the disc area. A normal cup-to-disc ratio is 0.3. A large cup-to-disc ratio (>0.5) may imply the onset of glaucoma. As such, the cup-to-disc ratio can be used for early detection of glaucoma. A processed image that outlines the disc (with the dotted line) is shown in FIG. 22B.

Figure 22C:
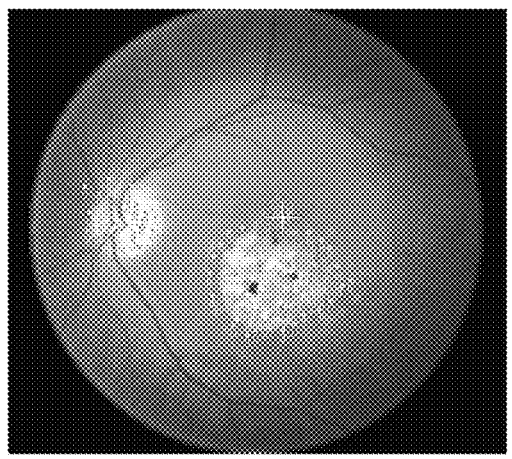

A data-fusion and analysis framework has been developed to normalize features extracted from a variety of image modalities, cluster them into meaningful groups in a unified feature space, and identify anomalies within (see, e.g., U.S. Pat. No. 9,122,956 and PCT/US2013/069517, both of which are hereby incorporated by reference in their entirety). The data fusion framework enables comparisons and correlations between data collected using different modalities and different functional tests over time. The framework has been proven on a variety of tasks, including space-based imagery analysis, visual field analysis, and retinal imaging. FIG. 22C shows an identification example of anomalies in a fundus image.

Figure 22D:
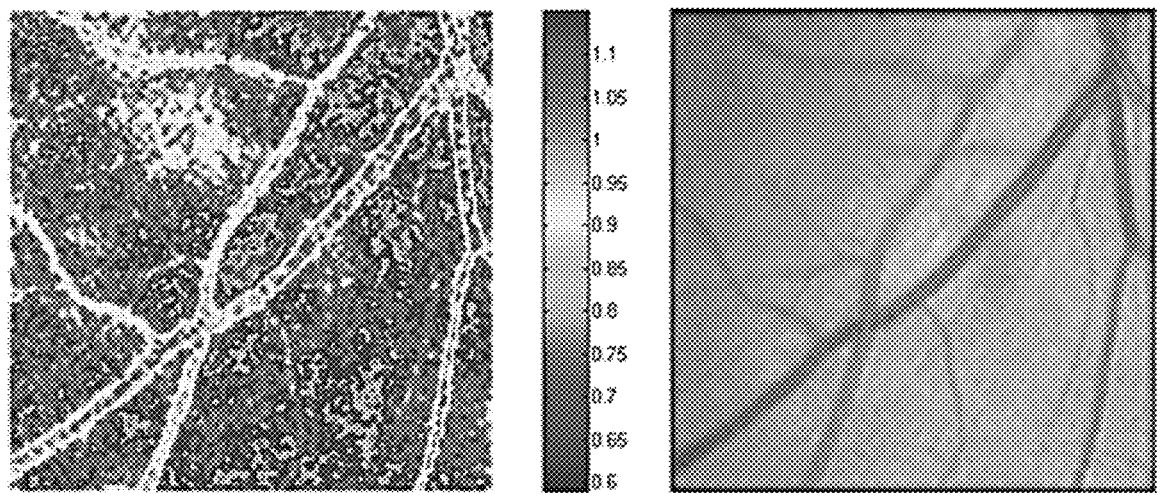
Figure 22E:
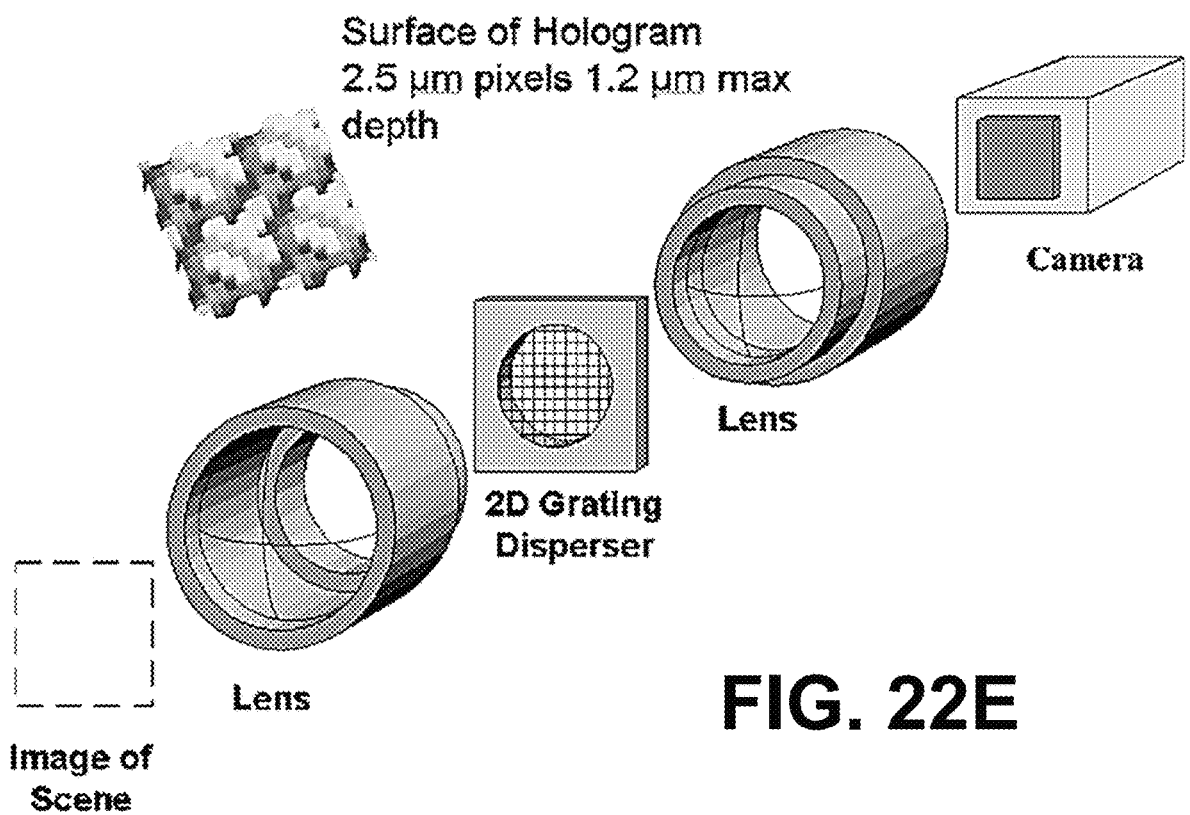
FIG. 22E illustrates a schematic example schematic of a hyperspectral camera that can be used in a smartphone according to various embodiments of the present disclosure.

Other ophthalmic examination modalities, such as retinal hyperspectral imaging, can also be considered. For instance, the use of snapshot hyperspectral imaging in ophthalmology in general and retinal imaging in particular can be implemented using Computed Tomography Imaging Spectrometer (CTIS) (see, e.g., "Snapshot hyperspectral imaging in ophthalmology" by Johnson et al., Journal of Biomedical Optics 12 (1), 014036 January/February 2007, which is hereby incorporated by reference in its entirety). Hyperspectral imaging offers functional rather than structural information, and provides complementary information for the clinician. Early results show how hemoglobin spectral signatures provide both qualitative and quantitative oxygen saturation maps of the retina. FIG. 22D shows an example of retinal oximetry (left) via analysis of a snapshot hyperspectral image of the fundus (right). Retinal hyperspectral imaging (HSI) offers the ability to capture in vivo metabolic and physiologic information using chromophore spectra to classify tissues and quantify cellular metabolites. Moreover, hyperspectral imaging holds great promise for the early detection of highly prevalent retinal vascular diseases, such as diabetic retinopathy and age-related macular degeneration—leading causes of untreatable blindness. These data offer the possibility of monitoring retinal ischemia from either systemic diseases such as diabetes or from localized retinal arterial and vascular occlusions—the leading causes of untreatable blindness. Retinal HSI offers the ability to capture in vivo metabolic and physiologic information using chromophore spectra to classify tissues and quantify cellular metabolites. FIG. 22E shows an example of a system that can be used to implement hyperspectral imaging.

Moreover, HSI holds great promise for the early detection of highly prevalent retinal vascular diseases. These include retinal disorders such as diabetic retinopathy, age-related macular degeneration, myopic degeneration, central and branch retinal vein occlusions, sickle-cell retinopathy among others. In our current world, both diabetes mellitus and age-related macular degeneration have reached epidemic proportions. Currently, it is estimated that over 30 million patients suffer from age-related macular degeneration worldwide. In addition, over 90 million patients are afflicted with diabetic retinopathy among the 330 million patients with diabetes mellitus world-wide. The current standards of diagnostic techniques for the evaluation of retinal disorders in ophthalmologic clinical practice are optical coherence tomography (OCT) and fluorescein angiography (FA). These diagnostic tools reveal exquisite detail about the anatomic deficits within the retinal and choroidal tissues during these disease processes that cause for vision to be reduced. However, these characteristics appear after destruction of the retinal tissue has occurred when it is often too late for treatments to restore photoreceptor function. These technologies give minimal information about the hypoxic states of these retinal structures that ultimately lead to the deleterious anatomic consequences. In contrast, HSI offers a novel non-invasive method to study the oxygenation states of retinal circulations and retinal tissue. The incorporation of the proposed snapshot HSI and its integration with a traditional fundus camera can bring this technology to everyday ophthalmic practice. The captured spectral signatures of oxygenated and deoxygenated hemoglobin offer the capability to generate unique in-vivo spectral 'fingerprint' signatures for specific retinal diseases. This technology will allow us to identify patients early on in the disease processes for treatment before they develop more deleterious forms of these disorders.

Figure 23:
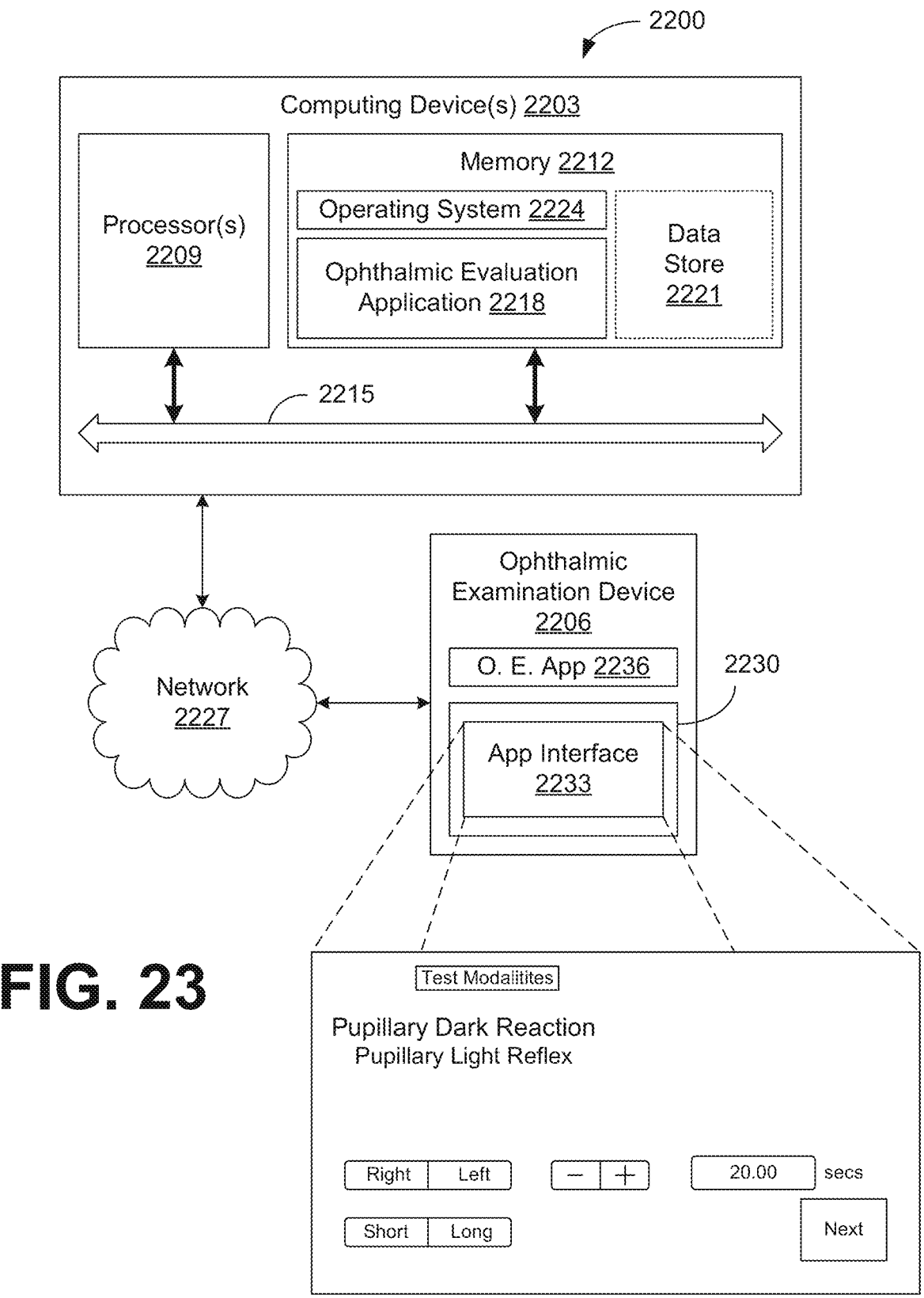
FIG. 23 is an example of a system that may be utilized in the ophthalmic examinations according to various embodiments of the present disclosure.

Referring now to FIG. 23, shown is an example of a system 2200 that may be utilized in ophthalmic examinations. The system 2200 includes one or more computing device(s) 2203 and one or more smartphone-based handheld ophthalmic examination device(s) 2206. The computing device 2203 includes at least one processor circuit, for example, having a processor 2209 and a memory 2212, both of which are coupled to a local interface 2215. To this end, the computing device(s) 2203 may comprise, for example, a server computer or any other system providing computing capability. The computing device(s) 2203 may include, for example, one or more display devices such as cathode ray tubes (CRTs), liquid crystal display (LCD) screens, gas plasma-based flat panel displays, LCD projectors, or other types of display devices, etc. The computing device(s) 2203 may also include, for example various peripheral devices. In particular, the peripheral devices may include input devices such as, for example, a keyboard, keypad, touch pad, touch screen, microphone, scanner, mouse, joystick, or one or more push buttons, etc. Even though the computing device 2203 is referred to in the singular, it is understood that a plurality of computing devices 2203 may be employed in the various arrangements as described above. The local interface 2215 may comprise, for example, a data bus with an accompanying address/control bus or other bus structure as can be appreciated.

Stored in the memory 2212 are both data and several components that are executable by the processor 2209. In particular, stored in the memory 2212 and executable by the processor 2209 are an ophthalmic evaluation application 2218 and potentially other applications. Also stored in the memory 2212 may be a data store 2221 and other data. The data stored in the data store 2221, for example, is associated with the operation of the various applications and/or functional entities described below. For example, the data store may include sample analysis results, corrective measures, and other data or information as can be understood. In addition, an operating system 2224 may be stored in the memory 2212 and executable by the processor 2209. The data store 2221 may be may be located in a single computing device or may be dispersed among many different devices.

The handheld ophthalmic examination device 2206 is representative of a plurality of user devices that may be communicatively coupled to the computing device 2203 through a network 2227 such as, e.g., the Internet, intranets, extranets, wide area networks (WANs), local area networks (LANs), wired networks, wireless networks, optical networks, cellular networks, networks configured for communication over a power grid, or other suitable networks, etc., or any combination of two or more such networks. In some embodiments, an ophthalmic examination device 2206 may be directly connected to the computing device 2203.

The handheld ophthalmic examination device 2206 may comprise, for example, a processor-based system such as a user device. Such a user device may be embodied in the form of a smartphone, tablet, or other devices with like capability. The user device 2206 includes a display 2230 upon which various app interfaces 2233, network pages, and other content may be rendered. The user device 2206 may be configured to execute various applications such as an ophthalmic examination app 2236 and/or other applications. The ophthalmic examination app 2236 may be executed in a user device 2206 such as a smartphone or tablet, for example, to access and render an app interface 2233, web pages, or other network content served up by the computing device 2203 and/or other servers. The ophthalmic examination device 2206 may be configured to execute applications beyond the ophthalmic examination app 2236 such as, for example, e-mail applications, instant message (IM) applications, voice mail, audio recording transmissions, phone call applications and/or other applications.

The components executed on the computing device 2203 include, for example, an ophthalmic evaluation application 2218 and other systems, applications, services, processes, engines, or functionality not discussed in detail herein. The ophthalmic evaluation application 2218 can generate information that can be displayed via the app interface 2233, such as evaluation content that is provided to the ophthalmic examination device 2206 in response to a request for the purpose of evaluating ophthalmic images acquired using the ophthalmic evaluation device 2206. An example of an app interface for "pupillary dark reaction" recording or measurement is illustrated in FIG. 23.

It is understood that there may be other applications that are stored in the memory 2212 and are executable by the processor 2209 as can be appreciated. Where any component discussed herein is implemented in the form of software, any one of a number of programming languages may be employed such as, for example, C, C++, C #, Objective C, Java, Java Script, Perl, PHP, Visual Basic, Python, Ruby, Delphi, Flash, or other programming languages.

A number of software components are stored in the memory 2212 and are executable by the processor 2209. In this respect, the term "executable" means a program file that is in a form that can ultimately be run by the processor 2209. Examples of executable programs may be, for example, a compiled program that can be translated into machine code in a format that can be loaded into a random access portion of the memory 2212 and run by the processor 2209, source code that may be expressed in proper format such as object code that is capable of being loaded into a random access portion of the memory 2212 and executed by the processor 2209, or source code that may be interpreted by another executable program to generate instructions in a random access portion of the memory 2212 to be executed by the processor 2209, etc. An executable program may be stored in any portion or component of the memory 2212 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 2212 is defined herein as including both volatile and nonvolatile memory and data storage components. Volatile components are those that do not retain data values upon loss of power. Nonvolatile components are those that retain data upon a loss of power. Thus, the memory 2212 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (M RAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 2209 may represent multiple processors 2209 and the memory 2212 may represent multiple memories 2212 that operate in parallel processing circuits, respectively. In such a case, the local interface 2215 may be an appropriate network that facilitates communication between any two of the multiple processors 2209, between any processor 2209 and any of the memories 2212, or between any two of the memories 2212, etc. The local interface 2215 may comprise additional systems designed to coordinate this communication, including, for example, performing load balancing. The processor 2209 may be of electrical or of some other available construction.

Although the ophthalmic evaluation application 2218 and ophthalmic examination app 2236, and other various systems described herein, may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The flowcharts of FIGS. 10A, 10B, 14, 19 and 21 show the functionality and operation of an implementation of portions of the ophthalmic evaluation application 2218 and/or ophthalmic examination app 2236. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 2209 in a computer system or other system. The machine code may be converted from the source code, etc. If embodied in hardware, each block may represent a circuit or a number of interconnected circuits to implement the specified logical function(s).

Although the flowcharts of FIGS. 10A, 10B, 14, 19 and 21 show a specific order of execution, it is understood that the order of execution may differ from that which is depicted. For example, the order of execution of two or more blocks may be scrambled relative to the order shown. Also, two or more blocks shown in succession in FIGS. 10, 14, 19 and/or 21 may be executed concurrently or with partial concurrence. Further, in some embodiments, one or more of the blocks shown in FIGS. 10A, 10B, 14, 19 and/or 21 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure. Other modules may also be included.

Also, any logic or application described herein, including the ophthalmic evaluation application 2218 and/or ophthalmic examination app 2236, that comprises software or code can be embodied in any non-transitory computer-readable medium for use by or in connection with an instruction execution system such as, for example, a processor 2209 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A handheld ophthalmic examination system, comprising:
   a handheld user device comprising a camera incorporated in the handheld user device;
   an optical imaging assembly comprising optics and a light source, the optical imaging assembly coupled to and supported by the handheld user device, the optical imaging assembly configured for at least one of pupillometer examination of an eye, slit lamp examination of the eye, Scheimpfluq imaging of the eye, stereo imaging of the eye, or hyperspectral imaging of the eye, where the camera of the handheld user device is aligned with the optics of the optical imaging assembly when the optical imaging assembly is coupled to the handheld user device thereby allowing imaging of the eye by the camera of the handheld user device,
   where the handheld user device is configured to:
      obtain ocular imaging data of at least a portion of the eye by the camera via the optics of the optical imaging assembly for the pupillometer examination of the eye, the slit lamp examination of the eye, the Scheimpfluq imaging of the eye, the stereo imaging of the eye, or the hyperspectral imaging of the eye, and
      provide ophthalmic evaluation results determined using the ocular imaging data.

2. The handheld ophthalmic examination system of claim 1, wherein the handheld user device is a smartphone.

3. The handheld ophthalmic examination system of claim 1, wherein the light source comprises a slit lamp supported by the handheld user device for slit lamp examination of the eye.

4. The handheld ophthalmic examination system of claim 1, wherein the optical imaging assembly is configured for pupillometer examination of the eye, the light source of the optical imaging assembly comprising a combination of near infrared and visible light diodes.

5. The handheld ophthalmic examination system of claim 1, wherein the optical imaging assembly is configured for stereo imaging of the eye, the optical imaging assembly comprising a mirror positioned for stereo imaging of the eye in a single captured image.

6. The handheld ophthalmic examination system of claim 1, wherein the optical imaging assembly is further configured for microscopic examination of the eye.

7. The handheld ophthalmic examination system of claim 1, wherein the ocular imaging data is an ocular image.

8. The handheld ophthalmic examination system of claim 7, wherein the ophthalmic evaluation results are based at least in part upon a portion of the ocular image.

9. The handheld ophthalmic examination system of claim 7, wherein the handheld user device is configured to provide the ocular image to a computing device for ophthalmic evaluation of the ocular image and receive the ophthalmic evaluation results from the computing device.

10. The handheld ophthalmic examination system of claim 9, wherein the handheld user device provides the ocular image to the computing device via a wireless network link.

11. The handheld ophthalmic examination system of claim 10, wherein the wireless network link is a cellular data link.

12. The handheld ophthalmic examination system of claim 9, wherein the computing device is a remotely located server.

13. The handheld ophthalmic examination system of claim 1, wherein the handheld user device is configured to obtain a plurality of ocular images.

14. The handheld ophthalmic examination system of claim 13, wherein the ophthalmic evaluation results are based at least in part upon a portion of the plurality of ocular images.

15. The handheld ophthalmic examination system of claim 13, wherein the plurality of ocular images is a series of ocular images.

16. The handheld ophthalmic examination system of claim 1, wherein the optical imaging assembly is detachably affixed to a casing coupled to the handheld user device.

17. The handheld ophthalmic examination system of claim 7, wherein the handheld user device is configured to process the ocular image.

18. A handheld ophthalmic examination system, comprising:
a handheld user device comprising a camera incorporated in the handheld user device:
an optical imaging assembly comprising optics and a light source, the optical imaging assembly coupled to and supported by the handheld user device, wherein the optical imaging assembly is configured for fundoscope examination of an eye, where the camera of the handheld user device is aligned with the optics of the optical imaging assembly when the optical imaging assembly is coupled to the handheld user device thereby allowing imaging of the eye by the camera of the handheld user device, the optical imaging assembly comprising a focusing assembly that enables fundus imaging without mydriasis,
where the handheld user device is configured to:
obtain ocular imaging data of at least a portion of the eye by the camera via the optics of the optical imaging assembly for the fundoscope examination of the eye, and
provide ophthalmic evaluation results determined using the ocular imaging data.

19. The handheld ophthalmic examination system of claim 18, wherein the light source comprises a slit lamp supported by the handheld user device for slit lamp examination of the eye.

20. The handheld ophthalmic examination system of claim 18, wherein the optical imaging assembly is further configured for Scheimpflug imaging of the eye.

21. The handheld ophthalmic examination system of claim 18, wherein the optical imaging assembly is further configured for hyperspectral camera imaging of the eye.

22. A method for ophthalmic examination of a subject, the method comprising:
receiving, by a computing device, ocular imaging data of at least a portion of an eye of the subject, the ocular image data provided by an ophthalmic examination device that obtained the ocular imaging data, the ophthalmic examination device comprising:
a handheld user device comprising a camera incorporated in the handheld user device; and
an optical imaging assembly comprising optics and a light source, the optical imaging assembly coupled to and supported by the handheld user device, the optical imaging assembly configured for at least one of pupillometer examination of the eye, slit lamp examination of the eye, Scheimpfluq imaging of the eye, stereo imaging of the eye, or hyperspectral imaging of the eye, where the camera of the handheld user device is aligned with the optics of the optical imaging assembly when the optical imaging assembly is coupled to the handheld user device thereby allowing imaging of the eye by the camera of the handheld user device;
determining, by the computing device, at least one ophthalmic characteristic of the eye by analyzing the ocular imaging data received by the computing device;
determining a condition of the subject based at least in part upon the at least one ophthalmic characteristic; and
providing, by the ophthalmic examination device, evaluation results determined using the ocular imaging data.

23. The method of claim 22, further comprising providing the evaluation results to the ophthalmic examination device by the computing device, the handheld user device of the ophthalmic examination device configured to display the evaluation results, the evaluation results determined using the at least one ophthalmic characteristic.

24. The method of claim 22, wherein the ophthalmic examination device is a smartphone-based handheld ophthalmic examination device.

25. The method of claim 22, wherein the ocular image data comprises images of both eyes of the subject.

26. The method of claim 22, wherein the ocular image data comprises an image or a video of at least a portion of the eye.

* * * * *